United States Patent
Miyamoto et al.

(10) Patent No.: US 6,583,138 B1
(45) Date of Patent: Jun. 24, 2003

(54) HETEROCYCLIC-RING CONDENSED BENZOTHIAZINE COMPOUND

(75) Inventors: Mitsuaki Miyamoto, Ibaraki (JP); Tatsuya Yoshiuchi, Ibaraki (JP); Keizo Sato, Ibaraki (JP); Motohiro Soejima, Ibaraki (JP); Takashi Sato, Ibaraki (JP); Koichi Kikuchi, Ibaraki (JP); Hiroyuki Yoshimura, Ibaraki (JP); Katsuhiro Moriya, Ibaraki (JP); Yoshinori Sakuma, Ibaraki (JP); Shigeru Akasofu, Ibaraki (JP); Koji Yamada, deceased, late of Ibaraki (JP); by Sumiyo Yamada, legal representative, Ibaraki (JP); by Ryoko Yamada, legal representative, Tokyo (JP)

(73) Assignee: Eisai Co., Ltd., Tokyo (JP)

(*) Notice: Subject to any disclaimer, the term of this patent is extended or adjusted under 35 U.S.C. 154(b) by 0 days.

(21) Appl. No.: 09/622,458

(22) PCT Filed: Feb. 26, 1999

(86) PCT No.: PCT/JP99/00942

§ 371 (c)(1),
(2), (4) Date: Jan. 4, 2001

(87) PCT Pub. No.: WO99/43683

PCT Pub. Date: Sep. 2, 1999

(30) Foreign Application Priority Data

Feb. 27, 1998 (JP) .............................. 10-46683

(51) Int. Cl.[7] ................... C07D 513/04; C07D 279/00; C07D 221/00; C07D 333/00; A61K 31/54

(52) U.S. Cl. ................. 514/224.8; 514/225.2; 514/225.5; 514/225.8; 514/226.2; 544/32; 544/34; 544/35; 544/38; 544/39; 544/40; 544/41; 544/42; 544/43; 544/44; 544/45; 544/46

(58) Field of Search ............... 544/32, 34, 35, 544/37, 38, 39, 40, 41, 42, 43, 44, 45, 46; 514/224.8, 225.2, 225.5, 225.8, 226.2

(56) References Cited

FOREIGN PATENT DOCUMENTS

| | | |
|---|---|---|
| JP | 60115524 | 6/1985 |
| JP | 60155165 | 8/1985 |
| JP | 11100373 | 4/1999 |
| WO | 9733871 | 9/1997 |

OTHER PUBLICATIONS

Chemical Abstracts, No. 95250j, vol. 127, No. 7, Aug. 18, 1997; Swati et al., "Synthesis of some novel 1–azaphenothiazines and their mesoionics as analogs of potent CNS–depressants", p. 608.

Primary Examiner—Bruck Kifle
(74) Attorney, Agent, or Firm—Birch, Stewart, Kolasch & Birch, LLP

(57) ABSTRACT

The invention provides a novel heterocyclic ring condensed benzothiazine compound which is effective for prevention or remedy of disease, in which histamine, leukotriene and the like participate. The heterocyclic ring condensed benzothiazine compound of the present invention or a pharmacologically acceptable salt thereof is effective for prevention or remedy of disease, in which a chemical mediator, such as histamine, leukotriene and the like, participate, for example, asthma, allergic coryza, atopic dermatitis, hives, hay fever, gastrointestinal allergy, food allergy and the like. Further, the heterocyclic ring condensed benzothiazine compound of the present invention, its pharmacologically acceptable salt or hydrates thereof is represented by the following formula:

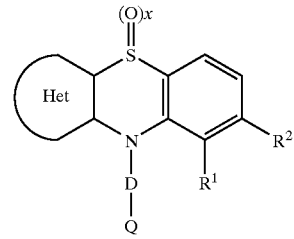

In the formula, the ring Het represents an unsaturated heterocyclic ring; $R^1$ and $R^2$ are the same as or different from each other, and each represents halogen atom, a lower alkyl group that may be substituted with a halogen atom, a lower alkoxy group that may be substituted with a halogen atom, a lower alkyl lower alkoxy group, cyano group; D represents a lower alkylene group and the like that may have a substituent; Q represents, for example, the formula —$NR^{20}R^{21}$ (in the formula, $R^{20}$ and $R^{21}$ are the same as or different from each other, and each represents hydrogen atom, a lower alkyl group that may be substituted with a halogen atom, an aryl group that may have a substituent, an arylalkyl group that may have a substituent, a heteroaryl group that may have a substituent or a heteroarylalkyl group that may have a substituent, or $R^{20}$ and $R^{21}$ may form a 3- to 8-membered ring along with the nitrogen atom to which they are bound); and x represents an integer of from 1 to 2.

31 Claims, No Drawings

HETEROCYCLIC-RING CONDENSED BENZOTHIAZINE COMPOUND

This application is the national phase under 35 U.S.C. §371 of PCT International Application No. PCT/JP99/00942 which has an International filing date of Feb. 26, 1999, which designated the United States of America.

FIELD OF THE INVENTION

The present invention relates to a heterocyclic ring condensed benzothiazine compound useful as a medicament, a medicament containing the same and processes for producing the same. More specifically, it relates to a novel heterocyclic ring condensed benzothiazine compound useful as a medicament for diseases against which the effect of inhibiting the binding of IgE receptor γ and a tyrosine kinase of 72 kDa is effective.

PRIOR ART

The bronchial asthma and the atopic diseases in human beings appear in consequence of highly intriacate vital reactions. It is suspected that most of these conditions are caused because various chemical mediators liberated from mast cells and basophils, as triggered by antigen-antibody reactions, induce vital disturbances as by contracting such smooth muscles as bronchial muscles and vessels of the pulmonary circulation or enhancing permeability of blood vessels.

As the chemical mediators liberated from mast cells and basophils, histamine, leukotrienes, prostaglandins, TNF, etc. have been known. It is well known that histamine, among other substances mentioned above, is the most significant chemical mediator for the allergic rhinitis and the urticaria in human beings. The leucotrienes comprise leucotrienes $B_4$, $C_4$, and $D_4$ and the relation thereof with the asthmatic convulsion has been attracting attention.

Heretofore, the development of medicines for the prevention, alleviation, or elimination of the symptoms of allergic diseases has been aimed at repressing the creation and liberation of such chemical mediators or antagonizing the effects thereof.

Sodium cromoglycate (Intal™) having been marketed since 1969 is a typical example of these drugs.

However, the conventional antiallergic agents typified by Intal™ show difference in the chemical mediator liberation inhibitory concentration between in vitro and in vivo. Moreover, sensitivities to these drugs widely vary from patient to patient and their action mechanisms still remain unknown in many points.

Mast cells and basophils closely relating to allergic diseases have a highly affinitive receptor, Fc ε RI, for the IgE antibody on the cell membrane thereof. IgE antibody's binding to this receptor forms a cross-linkage with the corresponding polyvalent antigen, the intracellular signal transmission mechanism is activated. Then histamine is liberated or leukotrienes and prostaglandins are formed and liberated, thus inducing the onset of the so-called allergic symptoms. It is furthermore considered that the cytokines such as TNF and interleukins thus produced interact with other cells and thus make the diseases chronic.

DISCLOSURE OF THE INVENTION

Under these circumstances, the present inventors have paid their attention to the activation of a non-receptor type tyrosine kinase located at the early stage in the activation of the intracellular signal transmission mechanism upon liberation of chemical mediators from mast cells or basophils. It is known that this tyrosine kinase is activated when it binds to the phosphorylated tyrosine activation motif (TAM) region in the IgE receptor γ chain. By inhibiting this binding to thereby inhibit the activation of the tyrosine kinase of 72 kDa, the activation of the intracellular signal transmission mechanism depending on the IgE antibody in mast cells or basophils can be inhibited. As a result, also the liberation of the above chemical mediators can be inhibited. The present inventors have found out that desired objects can be achieved by using heterocyclic ring condensed benzothiazine compounds represented by the following formula (I), thus completing the present invention.

WO97/33871 discloses a phenothiazine compound as a prophylactic or therapeutic agent for allergic disease of the similar mechanism, but does not disclose nor suggest a compound having a benzene ring containing a hetero atom.

An object of the invention is to provide a novel acridone compound which is effective for prevention or remedy of asthma, allergic coryza, atopic dermatitis, hives, hay fever, gastrointestinal allergy, food allergy and the like, and a pharmacologically acceptable salt thereof, and another object thereof is to provide a medicine containing, as an active ingredient, the compound, a hydrate thereof or a pharmacologically acceptable salt thereof.

That is, the invention is a heterocyclic ring condensed benzothiazine compound represented by the following formula (I), its pharmacologically acceptable salt or hydrates thereof. Formula (I)

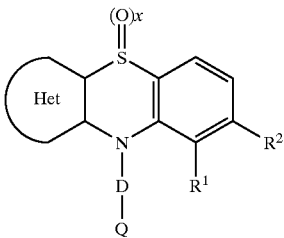

Wherein, the ring Het represents an unsaturated heterocyclic ring that may be substituted with from 1 to 3 substituents;

$R^1$ and $R^2$ are the same as or different from each other, and each represents halogen atom, a lower alkyl group that may be substituted with halogen, a lower alkoxy group that may be substituted with halogen, a lower alkoxy lower alkyl group, cyano group, carbamoyl group that may have a substituent or a carboxyl group that may have a protective group, and $R^1$ and $R^2$ may form a ring along with the carbon atom to which they are bound. The ring may contain oxygen atom, sulfur atom or nitrogen atom, and may have a substituent;

D represents a lower alkylene chain that may have a substituent, a lower alkenylene chain that may have a substituent, a lower alkynylene chain that may have a substituent or

(in the formula, m and 1 represent an integer of from 0 to 6, and the ring A represents a hydrocarbon ring that may have a substituent or a heterocyclic ring that may have a substituent)

Q represents carbamoyl group that may have a substituent, an acyl group, an acyl lower alkyl group, a carboxyl group that may have a protective group, a heteroaryl group that may have a substituent or a formula —$NR^{20}R^{21}$. In the formula —$NR^{20}R^{21}$, $R^{20}$ and $R^{21}$ are the same as or different from each other, and each represents hydrogen atom, a lower alkyl group that may be substituted with halogen, a lower alkoxy group that may be substituted with halogen, a lower alkyl group that is substituted with a hydroxyl group, a lower alkoxy lower alkyl group, an aryl group that may have a substituent, an aryl lower alkyl group that may have a substituent, a heteroaryl group that may have a substituent, a heteroaryl lower alkyl group that may have a substituent, an aryloxy group that may have a substituent, an aryl lower alkoxy group that may have a substituent, a heteroaryloxy group that may have a substituent, a heteroaryl lower alkoxy group that may have a substituent, a carboxyalkyl group that may have a protective group, an acyl group, an acyl lower alkyl group that may have a substituent, an acylamino group that may have a substituent, an acylamino lower alkyl group that may have a substituent, a carbamoyl lower alkyl group that may have a substituent, an amino lower alkyl group that may have a substituent, a cyano lower alkyl group, an acyl lower alkyl group, a lower cycloalkyl group, a lower cycloalkyl lower alkyl group or an amidino group that may be substituted with a lower alkyl group. Alternatively, $R^{20}$ and $R^{21}$ may form a 3- to 8-membered ring along with the nitrogen atom to which they are bound, and the ring may have, as a component constituting the ring, in addition to the carbon atoms at least one selected from the group consisting of a nitrogen atom, a sulfur atom, an oxygen atom and a formula —$NR^{22}$, and may have a substituent.

In the formula —$NR^{22}$, $R^{22}$ represents hydrogen atom, a lower alkyl group that may be substituted with halogen, an acyl group, an acyl lower alkyl group that may have a substituent, an aryl group that may have a substituent, a heteroaryl group that may have a substituent, an arylalkyl group that may have a substituent, a heteroarylalkyl group that may have a substituent or a formula

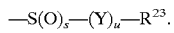
$$-S(O)_s-(Y)_u-R^{23}.$$

In the formula —$S(O)_s$—$(Y)_u$—$R^{23}$, $R^{23}$ represents hydrogen atom, a lower alkyl group that may be substituted with halogen or an aryl group that may have a substituent, Y represents a methylene chain, s represents an integer of from 0 to 2, and u represents 0 or 1); and x represents an integer of from 0 to 2.

The present invention provides a tyrosine kinase inhibitor, a preventive or therapeutic agent for disease, against which a tyrosine kinase inhibiting action is effective, an antiallergenic drug, a preventive or therapeutic agent for disease, against which an antiallergenic action is effective, or a preventive or therapeutic agent for asthma, allergic coryza, atopic dermatitis, hay fever, allergic conjunctivitis and food allergy, which comprises the heterocyclic ring condensed benzothiazine compound represented by the above formula (I) its pharmacologically acceptable salt or hydrates thereof as an active ingredient.

The present invention provides a method and a use for inhibiting tyrosine kinase, prevention or remedy of disease, against which a tyrosine kinase inhibiting action is effective, antiallergy, and disease, against which an antiallergenic action is effective, and prevention and remedy of asthma, allergic coryza, atopic dermatitis, hay fever, allergic conjunctivitis and food allergy, by administering a pharmacologically or clinically effective amount of the heterocyclic ring condensed benzothiazine compound represented by the above formula (I), its pharmacologically acceptable salt or hydrates thereof, to a patient infected with disease, against which tyrosine kinase inhibiting action is effective.

The present invention provides a medical composition containing a pharmacologically or clinically effective amount of the heterocyclic ring condensed benzothiazine compound represented by the formula (I), its pharmacologically acceptable salt or hydrates thereof, and a pharmacologically acceptable carrier.

DETAILED DESCRIPTION OF THE INVENTION

In the formula (I), the unsaturated hetero ring means a monocyclic heterocyclic ring, such as thiophene, furan, pyridine, pyrimidine, pyrazine, pyridazine and the like, or a bicyclic heterocyclic ring, such as quinoline, isoquinoline, naphthyridine.

The halogen atom found in the definition of $R^1$ and $R^2$ means fluorine, chlorine, bromine and iodine.

The lower alkyl group in the lower alkyl group that may be substituted with halogen found in the definition of $R^1$, $R^2$ $R^{22}$ and $R^{23}$ means a linear or branched alkyl group having from 1 to 6 carbon atoms. Examples thereof include methyl group, ethyl group, n-propyl group, isopropyl group, n-butyl group, isobutyl group, sec-butyl group, tert-butyl group, n-pentyl group, 1,2-dimethylpropyl group, 1,1-dimethylpropyl group, 2,2-dimethylpropyl group, 2-ethylpropyl group, n-hexyl group, 1,2-dimethylbutyl group, 2,3-dimethylbutyl group, 1,3-dimethylbutyl group, 1-ethyl-2-methylpropyl group, 1-methyl-2-ethylpropyl group and the like.

The language "may be substituted with halogen" herein means that the above alkyl groups may be substituted with from 1 to 3 halogen atoms, such as fluorine, chlorine, bromine and iodine. That is, trifluoromethyl group, dibromoethyl group and the like are included in the lower alkyl group that may be substituted with halogen in the formula (I).

The cycloalkyl group of the cycloalkyl group that may have a substituent found in the definition of $R^{20}$ and $R^{21}$ means those having from 3 to 8 carbon atoms, such as cyclopropyl group, cyclobutyl group, cyclopentyl group, cyclohexyl group, cycloheptyl group and cyclooctyl group.

The cycloalkylalkyl group found in the definition of $R^{20}$ and $R^{21}$ means those wherein the above cycloalkyl group is attached to any carbon atom of the above lower alkyl group.

The lower alkoxy group of the lower alkoxy group that may be substituted with halogen found in the definition of $R^1$, $R^2$ $R^{20}$ and $R^{21}$ means a linear or branched alkoxy group having from 1 to 6 carbon atoms. Examples thereof include methoxy group, ethoxy group, n-propoxy group, isopropoxy group, n-butoxy group, sec-butoxy group, tert-butoxy group, n-pentyloxy group,. 1,2-dimethylpropyloxy group, 1,1-dimethylpropyloxy group, 2,2-dimethylpropyloxy group, 2-ethylpropyloxy group, n-hexyloxy group, 1,2-dimethylbutyloxy group, 2,3-dimethylbutyloxy group, 1,3-dimethylbutyloxy group, 1-ethyl-2-methylpropyloxy group, 1-methyl-2-ethylpropyloxy group and the like.

The term "may be substituted with halogen" herein means that the above alkoxy group may be substituted with from 1 to 3 halogen atoms, such as fluorine, chlorine, bromine, iodine. That is, trifluoromethoxy group, dibromoethoxy group and the like are also included in the lower alkoxy group that may be substituted with halogen in the present invention.

The acyl group found in the definition of $R^{20}$, $R^{21}$ and $R^{22}$ means a group derived from an aliphatic saturated monocarboxylic acid, such as acetyl group, propyonyl group, butyryl group, valeryl group, isovaleryl group, pivaloyl group and the like, a group derived from an aliphatic unsaturated carboxylic acid, such as acryloyl group, propyoloyl group, methacryloyl group, crotonoyl group, isocrotonoyl group and the like, a group derived from a carbocyclic carboxylic acid, such as benzoyl group, naphthoyl group, toluoyl group, hydroatropoyl group, atropoyl group, cinnamoyl group and the like, a group derived from a heterocyclic carboxylic acid, such as furoyl group, thenoyl group, nicotinoyl group, isonicotinoyl group and the like, a group derived from a hydroxycarboxylic acid or an alkoxycarboxylic acid, such as glycoloyl group, lactoyl group, glyceloyl group, tropoyl group, benzyloyl group, salicyloyl group, anisoyl group, vanilloyl group, piperonyloyl group, galloyl group and the like, and a group derived from various amino acids.

The acylalkyl group found in the definition of $R^{20}$, $R^{21}$ and $R^{22}$ means those wherein the acyl group defined above is attached to any carbon atom of the lower alkyl group defined above. Examples thereof include acetylmethyl group, propyonylmethyl group, benzoylethyl group, naphthoylpropyl group, cinnamoylpropyl group, saliciloylbutyl group, nicotinoylpentyl group, glyceloylhexyl group and the like, but it is not limited thereto.

The alkoxyalkyl group found in the definition of $R^1$, $R^2$, $R^{20}$ and $R^{21}$ means those wherein the lower alkoxy group defined above is attached to any carbon atom of the lower alkyl group defined above. It means methoxymethyl group, ethoxymethyl group, ethoxyethyl group, 2-ethoxypropyl group and the like, but is not limited thereto.

The cyanoalkyl group found in the definition of $R^{20}$, $R^{21}$, $R^{22}$ and $R^{23}$ means those wherein the cyano group is attached to any carbon atom of the lower alkyl group defined above. It means cyano methyl group, 1-cyanoethyl group, 2-cyanoethyl group, 1-cyanopropyl group, 2-cyanopropyl group and the like.

The aryl group of the aryl group that may have a substituent found in the definition of $R^{20}$, $R^{21}$, $R^{22}$ and $R^{23}$ means phenyl group, 1-naphthyl group, 2-naphthyl group, anthracenyl group and the like.

The aryl of the arylalkyl group that may have a substituent found in the definition of $R^{20}$, $R^{21}$ and $R^{22}$ has the same meaning as the above aryl group. The alkyl group in this case has the same meaning as the above lower alkyl group.

The heteroaryl group that may have a substituent found in the definition of $R^{20}$, $R^{21}$ and $R^{22}$ means a group derived from a monocyclic ring or a condensed ring containing from 1 to 4 of at least one selected from the group consisting of a sulfur atom, an oxygen atom and a nitrogen atom. Examples thereof include pyrrolyl group, thienyl group, furyl group, thiazolyl group, oxazolyl group, isothiazolyl group, isoxazolyl group, imidazolyl group, pyrazolyl group, thiadiazolyl group, oxadiazolyl group, triazolyl group, tetrazolyl group, pyridyl group, a pyridazinyl group, a pyrimidinyl group, a pyrazinyl group, an indolyl group, an isoindolyl group, a benzothienyl group, a benzofuranyl group, an isobenzofuranyl group, a benzoimidazolyl group, an indazolyl group, a benzotriazolyl group, a benzothiazolyl group, a benzooxazolyl group, a quinolyl group, an isoquinolyl group, a cinnolinyl group, a phthalazyl group, a quinoxalyl group, a naphthyridyl group, a quinazolyl group, an imidazopyridyl group and the like.

The heteroarylakyl group that may have a substituent found in the definition of $R^{20}$, $R^{21}$ and $R^{22}$ means those wherein the above heteroaryl is attached to any carbon atom of the above lower alkyl group.

The carbamoyl group that may have a substituent found in the definition of $R^1$ and $R^2$ means carbamoyl group having one or two substituents on the nitrogen atom thereof.

The substituent of the unsaturated heterocyclic ring that may be substituted with from 1 to 3 substituents, the aryl group that may have a substituent, the heteroaryl group that may have a substituent, the arylalkyl group that may have a substituent, the heteroarylalkyl group that may have a substituent, the heteroarylalkynyl group that may have a substituent, the arylalkoxy group that may have a substituent, the heteroarylalkoxy group that may have a substituent and the carbamoyl group that may have a substituent means hydroxyl group, a lower alkyl group, such as methyl, ethyl, n-propyl, isopropyl and the like, a lower alkoxy group, such as methoxy, ethoxy, n-propoxy, isopropoxy and the like, a halogen atom, such as a fluorine atom, a chlorine atom, a bromine atom, an iodine atom and the like, cyano group, an acyl group, such as anacetyl group, a propyonyl group, a benzoyl group and the like, amino group, nitro group, a carboxyl group that may have a protective group, carbamoyl group, an acylamino group, a sulfamoyl group, an alkylsulfonylamino group, an arylsulfonylamino group, a heteroaryl group, a carboxyalkyl group, a carboxyalkoxy group, a heteroarylalkyl group, a heteroarylalkoxy group, a methylenedioxy group, an ethylenedioxy group and the like, and selected from them.

The protective group of the carboxyl group that may have a protective group found in the definition of $R^1$, $R^2$, $R^{20}$ and $R^{21}$ means, for example, a lower alkyl group, such as methyl group, ethyl group, tert-butyl group and the like, a lower alkyl group substituted with a phenyl group that may have a substituent, such as p-methoxybenzyl, p-nitrobenzyl, 3,4-dimethoxybenzyl, diphenylmethyl, trityl, phenethyl and the like, a halogenated lower alkyl group, such as 2,2,2-trichloroethyl, 2-iodoethyl and the like, a lower alkanoyloxy lower alkyl group, such as pivaloyloxymethyl, acetoxymethyl, propyonyloxymethyl, butyryloxymethyl, valeryloxymethyl, 1-acetoxyethyl, 2-acetoxyethyl, 1-pivaloyloxyethyl, 2-pivaloyloxyethyl and the like, a higher alkanoyloxy lower alkyl group, such as palmitoyloxyethyl, heptadecanoyloxymethyl, 1-palmitoyloxyethyl and the like, a lower alkoxycarbonyloxy lower alkyl group, such as methoxycarbonyloxymethyl, 1-butoxycarbonyloxyethyl, 1-(isopropoxycarbonyloxy)ethyl and the like, a carboxy lower alkyl group, such as carboxymethyl, 2-carboxyethyl and the like, a heteroaryl group, such as 3-phthalidyl and the like, a benzoyloxy lower alkyl group that may have a substituent, such as 4-glycyloxybenzoyloxymethyl and the like, a substituted dioxolene lower alkyl group, such as (5-methyl-2-oxo-1,3-dioxolene-4-yl)methyl and the like, a cycloalkyl-substituted lower alkanoyloxy lower alkyl group, such as 1-cyclohexylacetyloxyethyl and the like, and a cycloalkyloxycarbonyloxy lower alkyl group, such as 1-cyclohexyloxycarbonyloxyethyl and the like. Furthermore, it may be various acid amides. In its essence, any one can be the protective group of a carboxyl group as far as it can be a carboxylic acid by decomposition in vivo through some measures.

The ring in the term "$R^{20}$ and $R^{21}$ may form a ring along with the nitrogen atom to which they are bound" in the formula —$NR^{20}R^{21}$ found in the definition of Q means aziridine, azetidine, pyrrolidine, piperidine, perhydroazepine, perhydroazocine, piperazine, homopiperazine, morpholine, thiomorpholine, thiomorpholinedioxide, indoline, isoindoline, 1,2,3,4-tetrahydroquinoline, 1,2,3,4-tetrahydroisoquinoline, 2,3-dihydrobenzooxazine, 2,3-dihydrobenzothiadine, pyrrole, imidazole, pyrazole, triazole, tetrazole, indole, isoindole, indazole, benzotriazole and the like.

It is needless to say that the compounds having an asymmetric atom in the present invention, optical isomers thereof are also included in the invention. The present invention further includes the compounds of the present invention that are formed in vivo through metabolism.

The pharmacologically acceptable salt in the present invention includes, for example, an inorganic salt, such as a hydrochlorate, a hydrobromate, a sulfate, a phosphate and the like, an organic acid salt, such as an acetate, a maleate, a tartarate, a methanesulfonate, a benzenesulfonate, a toluenesulfonate and the like, and a salt formed with an amino acid, such as asparaginic acid, glutamic acid and the like.

The compounds of the present invention can be produced in such a manner that a heterocyclic ring condensed benzothiazine skeleton is produced by utilizing Smiles rearrangement reaction or Ullmann reaction of a heterocyclic ring-S-benzene ring compound obtained by a known method, and the —D—Q side chain (in the formula, D and Q have the above meanings) is introduced to the NH group thus formed by a generally known method (for example, WO97/33871). Major general production reaction schemes of the compounds of the present invention will be shown below.

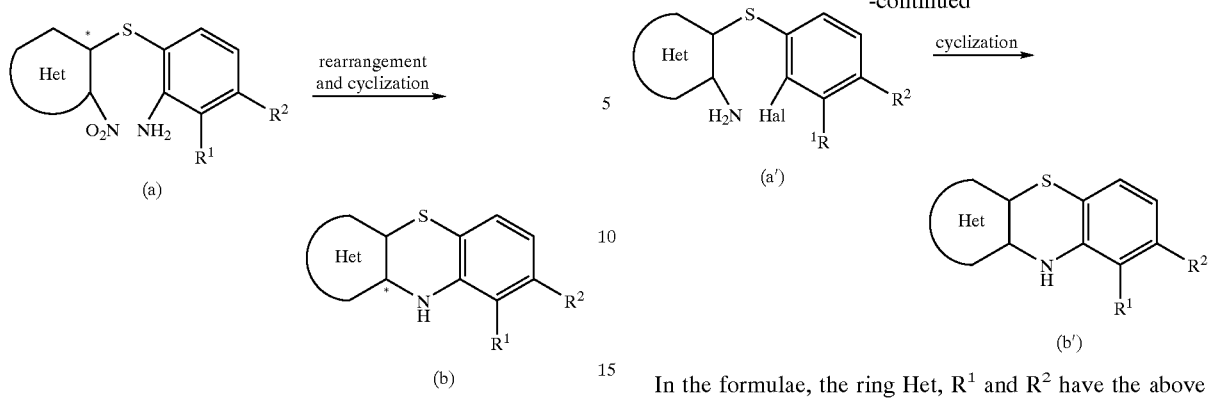
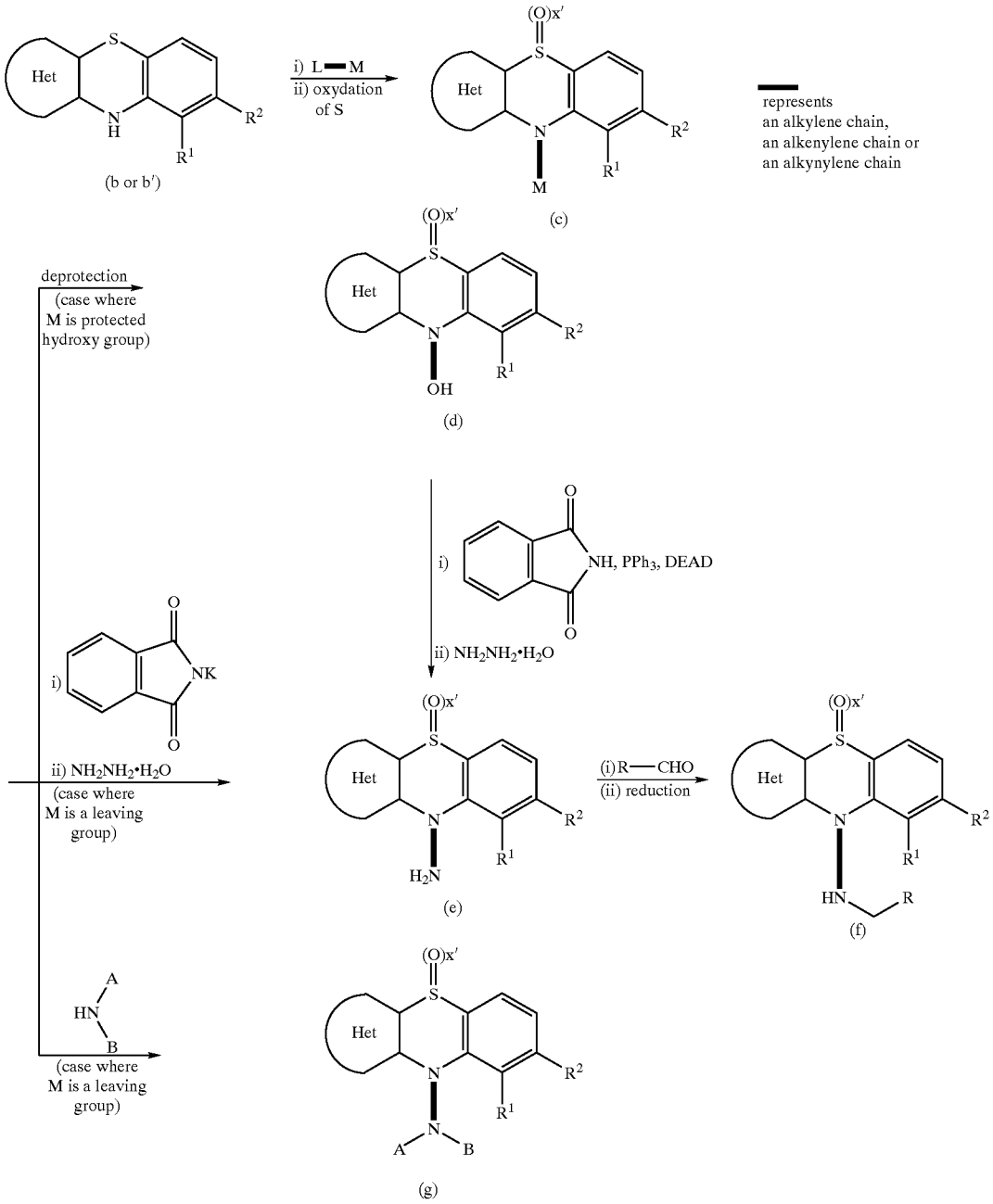
In the formulae, the ring Het, $R^1$ and $R^2$ have the above meanings, and Hal represents chlorine, bromine or iodine.

In the formulae, L represents a leaving group, M represents hydroxyl group that may have a leaving group or a protective group, and x' represents an integer of 1 or 2. R represents a lower alkyl group, an aryl group that may have a substituent, a heteroaryl group that may have a substituent, an aryl lower alkyl group that may have a substituent or a heteroaryl lower alkyl group that may have a substituent. A and B are the same as or different from each other, and each represents hydrogen atom, a lower alkyl group, an aryl lower alkyl group that may have a substituent or a heteroaryl lower alkyl group that may have a substituent. The ring Het, $R^1$ and $R^2$ have the above meanings.

The benzothiazine compound (b or b') obtained in Production Method 1 and a compound having at both ends thereof hydroxyl groups that may have a leaving group or both a leaving group and a protective group are reacted in the presence of a base, to obtain a benzothiazine compound represented by the formula (c). In this case, preferred examples of the base include potassium carbonate, sodium hydride, n-butyl lithium, t-butoxy potassium and the like. Preferred examples of the leaving group herein include halogen, sulfonate and the like. Examples of the protective group of the hydroxyl group include t-butyldimethylsilyl group, tetrahydropyranyl group and the like. As a reaction solvent, any one that does not participate in the reaction can be used. It is then treated with m-chloroperbenzoic acid (MCPBA) in methylene chloride, with monopersusfate (potassium peroxymonosulfate) in a mixed solvent of methanol and water, or with hydrogen peroxide in acetic acid, to obtain an oxide or a dioxide.

Next, in the case where M is hydroxyl group that may have a protective group, and for example in the case of hydroxyl group protected by a t-butyldimethylsilyl group, it is treated with tetrabutylammoniumfluoride in a solvent, such as tetrahydrofuran and the like, to form an alcohol (d), and then treated with a hydrazine hydrate to obtain an amine (e). In the case where M is a leaving group, the amine can also be obtained in the same manner by treating with phthalimide potassium. The amine (e) and an aldehyde compound are subjected to dehydration condensation to form Schiff base, which is treated with a reducing agent, such as sodium boron hydride and the like, to obtain an amine compound represented by the formula (f). As the reaction solvent, any one that does not participate in the reaction can be used.

Furthermore, in the case where M is a leaving group, a secondary or tertiary amine compound (g) can be obtained by acting a primary or secondary amine.

Resolution of optical isomers is conducted by chiral column chromatography or by fractional recrystallization of a salt with an optically active organic acid or organic amine.

Next, to describe the usefulness of the present invention, Pharmacological Experimental Examples will be shown below.

PHARMACOLOGICAL EXPERIMENTAL EXAMPLES (1) Inhibitory Effects on Various Mediators Release from Rat Basophilic Leukemia Cell Line (RBL-2H3)

RBL-2H3cells (i.e., a cell line originating in rat cells), by stimulation with IgE sepecific antigen, not only release histamine and serotonin but also release and produce cytokines such as TNF α and prostaglandins which are inflammatory mediators. In this experimental system, inhibitory effects on various mediators release were examined by using serotonin as an indication.

The cells were beforehand labeled with [$^3$H]-labeled serotonin and, at the same time, sensitized with the IgE antibody. After incubating with the compounds of the present invention, they were stimulated with the specific antigen. Then the inhibitory activity of each compound was calculated from the amount of the [$^3$H]-labeled serotonin thus liberated into the medium due to the stimulation and the amount of [$^3$H]-labeled serotonin liberated when no compound of the present invention was added.

The results are shown in Table 1.

TABLE 1

| Ex.no. | IC$_{50}$ ($\mu$M) in serotonin liberation from RBL-2H3 cells | Ex.no. | IC$_{50}$ ($\mu$M) in serotonin liberation from RBL-2H3 cells |
|---|---|---|---|
| 1 | 2 | 26 | 2 |
| 3 | 8 | 31 | 2 |
| 4 | 2 | 33 | 2 |
| 5 | 6 | 34 | 5 |
| 6 | 2 | 35 | 3 |
| 7 | 2 | 36 | 4 |
| 8 | 1 | 37 | 3 |
| 9 | 0.5 | 38 | 4 |
| 10 | 0.5 | 39 | 3 |
| 11 | 5 | 40 | 4 |
| 12 | 4 | 41 | 3 |
| 13 | 3 | 42 | 4 |
| 15 | 0.5 | 43 | 2 |
| 16 | 2 | 44 | 2 |
| 17 | 2 | 45 | 1 |
| 18 | 2 | 46 | 2 |
| 19 | 1 | 47 | 3 |
| 20 | 5 | 48 | 4 |
| 24 | 4 | 49 | 2 |
| 25 | 2 | 52 | 3 |

The compound numbers in the table correspond to Example Nos. as will be given hereinafter (the same will apply hereinafter).

(2) Inhibitory Effects on Various Mediators Release from Human Basophils 6 ml of 6% dextran (for separating leukocytes, having a high molecular weight) was added to 20 ml of heparinized blood. After stirring well, the resulting mixture was allowed to stand at 37° C. for 30 min and thus erythrocytes were precipitated. The upper layer was taken up and phosphate buffered saline was added thereto followed by centrifugation at 185 g for 8 minutes to give a crude leukocyte fraction. These cells were subjected to hypotonic hematolysis and then suspended in D-PBS(+) containing 0.1%-BSA. The resulting suspension was used in the subsequent experiment as the leukocyte fraction containing basophils. 0.4 ml of this cell suspension was preliminarily heated to 37° C. for 5 min and then 0.05 ml of a specimen solution was added thereto followed by a pretreatment at 37° C. for 15 min. Next, 0.05 ml of a mite antigen solution was added thereto to induce an antigen-antibody reaction. After 10 min, the reaction was ceased by ice-cooling. Then the reaction mixture was centrifuged again at 185 g for 10 min and histamine and peptide leukotrienes in the resulting supernatant were determined by using enzyme immunoassay kits. From the results of the assay, the activities of the a heterocyclic ring condensed benzothiazine compound of inhibiting the liberation of histamine and peptide leukotriene were determined.

The results are given in Table 2, wherein the term "leukotriene" means peptide leukotriene.

TABLE 2

| | IC$_{50}$ ($\mu$M) in mediator liberation from human basophils | |
| Ex.no. | histamine | leukotriene |
| --- | --- | --- |
| 1 | 10–30 | 10 |
| 2 | 30 | 10–30 |
| 4 | 10–30 | 10 |
| 6 | 30 | 10–30 |
| 7 | 3–10 | 3–10 |
| 8 | 10 | 3 |
| 9 | 10–30 | 3 |
| 10 | 30 | 3–10 |
| 11 | 10 | 3 |
| 12 | 10 | 3 |
| 16 | 10 | 10–30 |
| 17 | 10–30 | 10–30 |
| 18 | 30 | 10–30 |
| 31 | 10–30 | 10 |
| 33 | 10–30 | 3–10 |
| 37 | 30 | 30 |
| 42 | 10–30 | 3 |
| 43 | 30 | 10 |
| 49 | 10–30 | 3 |
| 52 | 10–30 | 3 |

(3) Production of Passive Sensitization Rat Allergic Air Pouch Type Inflammation Model and Measurement of Action of Compound Rats (Sprague-Dawley series, male, 6 weeks) were anaesthetized with ether, and 6 ml of air is injected subcutaneously on a region of back to produce a circular or ovoid sape air pouch. 1 ml of mouse monoclonal anti-2,4-dinitrophenyl (DNP) IgE antibody was injected into the air pouch to subject the rats to passive sensitization. On the following day, the rats were anaesthetized with ether, and 0.9% physiological saline containing 1% Evans Blue dye and 1 mg/ml of DNP bovine serum albumin (DNP-BSA) was administered intravenously at a dose of 0.2 ml per 100 g body weight to initiate an allergic reaction. After 5 minutes, the rats were anaesthetized with ether, and 5 ml of 0.9% physiological saline containing 0.1% of bovine serum albumin was injected in the air pouch. After lightly kneading the air pouch, 2 ml of the physiological saline was collected. The amounts of histamine and peptide leukotriene in the collected physiological saline were measured by ELISA method.

The compound of the present invention was orally administered 30 minutes before the administration of DNP-BSA as an antigen, to examine the inhibitory action on the model.

The results are shown in Table 3.

TABLE 3

| Ex. No. | Inhibitory rate | |
| (Dose) | histamine | leukotriene |
| --- | --- | --- |
| 42 (10 mg/kg) | 60% | 70% |

Thus, the compounds of the present invention inhibit liberation of a chemical mediators, such as serotonin, histamine, leukotriene and the like, and the effect has been also confirmed in the inflammation model. Therefore, the compounds of the present invention can be used as a preventive or therapeutic agent for disease caused by liberation of a chemical mediators, such as serotonin, histamine, leukotriene and the like. More specifically, it is useful for prevention and remedy of allergic disease such as asthma, allergic coryza, atopic dermatitis, hives, hay fever, gastrointestinal allergy, food allergy and the like.

Moreover, the compounds of the present invention are useful from the viewpoint the low toxicity and high safety thereof.

When the compounds of the present invention are used for the above-mentioned diseases, they may be administered both orally and parenterally, and in the dosage form of tablets, powders, granules, capsules, syrups, troches, inhalants, suppositories, injections, ointments, ophthalmic ointments, eye drops, nasal drops, ear drops, cataplasmas, lotions, etc.

The administration dose widely varies depending on the type of the disease, the severity of the symptoms, the age, sex and drug sensitivity of the patient. In general, such a compound is administered in a daily dose of from about 0.03 to 1,000 mg, preferably from 0.1 to 500 mg and still preferably from 0.1 to 100 mg once to several times a day. In the case of injections, the dose usually ranges from about 1 $\mu$g/kg to 3,000 $\mu$g/kg, preferably from about 3 $\mu$g/kg to 1,000 $\mu$g/kg.

The compounds of the present invention may be processed into preparations by conventional methods with the use of conventional pharmaceutical carriers.

Namely, solid preparations for oral administration are prepared by mixing the principal agent with fillers, binders, disintegrating agents, lubricants, coloring agents, corrigents, antioxidants, etc. and then processed into tablets, coated tablets, granules, powders, capsules, etc. by conventional methods.

Examples of the above-mentioned fillers are lactose, corn starch, sucrose, glucose, sorbitol, crystalline cellulose, silicon dioxide, etc.

Examples of the binders are polyvinyl alcohol, polyvinyl ether, ethylcellulose, methylcellulose, acacia, tragacanth, gelatin, shellac, hydroxypropylcellulose, hydroxypropylmethylcellulose, calcium citrate, dextrin and pectin. Examples of the lubricants are magnesium stearate, talc, polyethylene glycol, silica, hardened vegetable oils, etc.

The coloring agents are those admitted to be added to medicines. Examples of the corrigents include cocoa powder, menthol, aromatic powder, peppermint oil, borneol and powdered cinnamon bark. As the antioxidants, use can be made of any pharmaceutically authorized ones such as ascorbic acid and α-tocopherol. Needless to say, tablets and granules may be appropriately coated with sugar, gelatin, etc., if necessary.

Meanwhile, injections, eye drops, etc. can be prepared by blending the principal agent with, if needed, pH regulating agents, buffer agents, suspending agents, dissolution aids, stabilizers, tonicity agents, antioxidants, preservatives, etc. and then processed in a conventional manner. In such a case, it is also possible, if needed, to give freeze-dried preparations. Injections may be intravenously, hypodermically or intramuscularly administered.

Examples of the above-mentioned suspending agents include methylcellulose, Polysorbate 80, hydroxyethylcellulose, acacia, tragacanth, sodium carboxymethylcellulose and polyoxyethyelne sorbitan monolaurate.

Examples of the dissolution aids are polyoxyethylene-hardened castor oil, Polysorbate 80, nicotinamide, polyoxyethylene sorbitan monolaurate, etc.

Examples of the stabilizers usable herein include sodium sulfite, sodium metasulfite and ether. Examples of the preservatives usable herein include methyl p-hydroxybenzoate, ethyl p-hydroxybenzoate, sorbic acid, phenol, cresol and chlorocresol.

Ointments can be produced by blending the principal agent with, if needed, stabilizers, antioxidants, preservatives, etc. and processed in a conventional manner.

EXAMPLES

To facilitate the understanding or the present invention, Examples will be given below, though it is needless to say that the present invention is not restricted thereto. Analogous compounds synthesized by similar procedures are listed in tables. The synthesized sulfoxide compounds are all mixtures of optical isomers. The $^1$H-NMR data sometimes do not involve active hydrogen in the compounds. In the table, each number given at the lower left of the structural formula means the Example number. Production Examples of the starting compounds of the compound of the present invention will be also given.

Production Example 1

3-Bromo-2-nitrothiophene

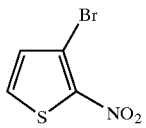

7.4 ml of fuming nitric acid was slowly added to 92.1 ml of acetic acid under ice-cooling, followed by stirring for 10 minutes, and a solution of 52.1 ml of acetic anhydride containing 25 g of 3-bromothiophene was slowly added in such a manner that the bulk temperature did not exceed 10° C., followed by stirring at 10 ° C. for 2 hours. Ice was added to the reaction solution, and the resulting crystals were collected by filtration, and washed with water and diethyl ether/n-hexane=1/5 successively, to give 17.4 g of the title compound.

$^1$H-NMR(400 MHz, CDCl$_3$) d; 7.49(d,J=6,1H), 7.11(d,J=6,1H)

Production Example 2

2-Amino-3,4-dimethylphenyl-2-nitro-3-thienylsulfide

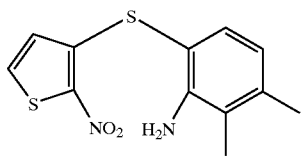

To a solution of 500 ml of N,N'-dimethylformamide containing 17.3 g of 3-bromo-2-nitrothiophene obtained in Production Example 1 and 12.7 g of 2-amino-3,4-dimethylthiophenol synthesized from 2,3-dimethylaniline by a method of a known literature (J. Org. Chem., 1984, 49, 997–1000), 23.0 g of potassium carbonate was added, followed by stirring at 80° C. for 10 hours. The reaction solution was diluted with water and extracted with ethyl acetate. The organic layer was washed with brine, dried over anhydrous magnesium sulfate, and then the solvent was evaporated to give 18.3 g of the title compound.

$^1$H-NMR(400 MHz, CDCl$_3$) d; 7.27(d, J=6,1H), 7.24(d, J=8, 1H), 6.66(d,J=8,1H), 6.24(d,J=6,1H), 4.29(bs,2H), 2.32 (s,3H), 2.04(s,3H).

Production Example 3

2-Formamide-3,4-dimethylphenyl-2-nitro-3-thienylsulfide

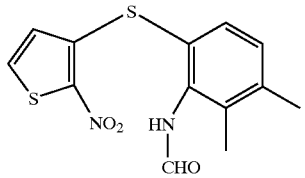

A solution of 183 ml of formic acid and 18.3 ml of water containing 18.3 g of 2-amino-3,4-dimethylphenyl-2-nitro-3-thienylsulfide obtained in Production Example 2 was heated under reflux for 14 hours.

The reaction solution was cooled to room temperature and poured onto ice, it was neutralized with sodium hydroxide aqueous solution and extracted with ethyl acetate. The organic layer was washed with brine, dried over anhydrous magnesium sulfate, and then the solvent was evaporated. The resulting crystals were washed with ethyl acetate/n-hexane=1/4, to give 11.2 g of the title compound.

$^1$H-NMR(400 MHz, CDCl$_3$) d; 8.23(s,1H), 7.46 (d,J=8, 1H), 7.32–7.22(m,2H), 6.19(d,J=8,1 H), 2.40(s,3H), 2.12(s, 3H).

Production Example 4

9-H-7,8-Dimethyl-3-thieno[1,4]benzothiazine

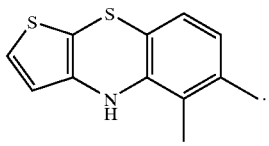

To a solution of 150 ml of acetone containing 3.0 g of 2-formamide-3,4-dimethylphenyl-2'-nitro-3'-thienylsulfide obtained in Production Example 3, 19.5 ml of a 1N potassium hydroxide ethanol solution was added, followed by heating under reflux for 3 hours. The solvent was evaporated. The resulting residue was purified by silica gel column chromatography to give 510 mg of the title compound.

$^1$HR-NMR(400 MHz, DMSO-d$_6$) d; 7.73(bs,1H), 7.28(d, J=5,1H), 6.81(d,J=5,1H), 6.62(d,J=8,1H), 6.60(d,J=8,1H), 2.12(s,3H), 2.04(s,3H).

Production Example 5

9-(3-Chloropropyl)-7,8-dimethyl-3-thieno[1,4]
benzothiazine

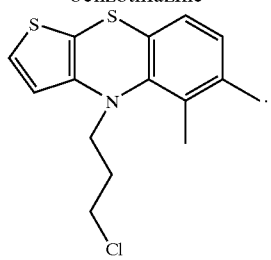

To a solution of 25 ml of N,N'-dimethylformamide containing 500 mg of 9-H-7,8-dimethyl-3-thieno[1,4] benzothiazine obtained in Production Example 4, 77 mg of sodium hydride was added under stirring at room temperature, and after stirring for 30 minutes, 0.25 ml of 1-chloro-3-iodopropane was added thereto, followed by stirring at room temperature for 20 hours. Water was added to the reaction solution, which was then extracted with diethyl ether. The organic layer was washed with brine, dried over anhydrous magnesium sulfate, and then the solvent was evaporated. The resulting residue was purified by silica gel column chromatography, to give 360 mg of the title compound.

$^1$H-NMR(400 MHz, CDCl$_3$) d; 7.12(d,J=6,1H), 6.87(d,J=8,1H), 6.84(d,J=8,1H), 6.74(d,J=6,1H), 3.59(t,J=7,2H), 3.53(t,J=7,2H), 2.26(s,3H), 2.24(s,3H), 2.13–2.04(m,2H).

Production Example 6

9-(3-Chloropropyl)-7,8-dimethyl-3-thieno[1,4]
benzothiazine-4-oxide

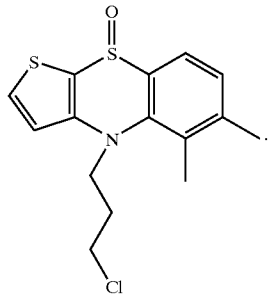

To a solution of 20 ml of dichloromethane containing 300 mg of 9-(3-chloropropyl)-7,8-dimethyl-3-thieno[1,4] benzothiazine obtained in Production Example 5, 98 mg of sodium hydrogen carbonate was added, followed by cooling to −40° C. 209 mg of m-chloroperbenzoic acid was slowly added thereto under stirring and stirred at −40° C. for 30 minutes. The reaction solution was poured into water and extracted with dichloromethane. The organic layer was washed with brine, dried over anhydrous magnesium sulfate, and then the solvent was evaporated. The resulting residue was purified by silica gel column chromatography, to give 251 mg of the title compound.

$^1$H-NMR(400 MHz, CDCl$_3$) d; 7.62(d,J=5,1H), 7.59(d,J=8,1H) 7.21(d,J=5,1H), 7.17(d,J=8,1H), 4.30(d,J=6,1H), 4.29(d,J=6,1H), 3.44(d,J=6,1H), 3.42(d,J=6,1H), 2.42(s,3H), 2.39(s,3H), 2.05–1.86(m,2H).

Example 1

9-(3-Benzylaminopropyl)-7,8-dimethyl-3-thieno [1,4]benzothiazine-4-oxide

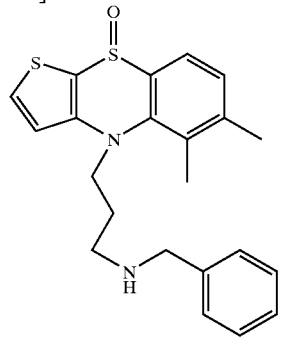

To a solution of 4 ml of toluene containing 39 mg of 9-(3-chloropropyl)-7,8-dimethyl-3-thieno[1,4] benzothiazine-4-oxide obtained in Production Example 6, 0.13 ml of benzylamine was added and heated under reflux for 20 hours. An ammonium chloride aqueous solution was added to the reaction solution, which was then extracted with ethyl acetate. The organic layer was washed with brine, dried over anhydrous magnesium sulfate, and then the solvent was evaporated. The resulting residue was purified by silica gel column chromatography, to give 38 mg of the title compound.

$^1$H-NMR(400 MHz, CDCl$_3$) d; 7.59(d,J=9,1H), 7.58(d,J=5,1H) 7.30–7.13(m,7H), 4.25–4.10(m,2H), 3.60(d,J=13,1H), 3.55(d,J=13,1H), 2.55–2.45(m,2H), 2.39(s,3H), 2.37(s,3H), 1.76–1.61(m,2H)

The following compound was obtained in the same manner as in Example 1.

TABLE 4

| Ex. No. | | $^1$H-NMR (400 MHz) δ |
|---|---|---|
| 2 | (structure) | CDCl3<br>7.59(d, J=8, 1H), 7.58(d, J=5, 1H), 7.36–7.32(m, 2H), 7.30–7.25(m, 2H), 7.21–7.18(m, 1H), 7.16(d, J=5, 1H), 7.14(d, J=8, 1H), 4.20–4.03(m, 2H), 2.38(s, 6H), 2.24–2.12(m, 2H), 1.70–1.52(m, 2H), 1.31(s, 3H), 1.28(s, 3H) |

Production Example 7

7,8-Dimethyl-9-(3-phthalminoproplyl)-3-thieono[1,4]benzothiazine-4-oxide

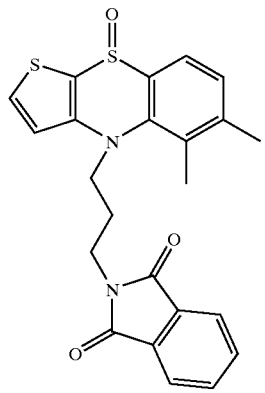

To a solution of 10 ml of N,N'-dimethylformamide containing 210 mg of 9-(3-chloropropyl)-7,8-dimethyl-3-thieno[1,4]benzothiazine-4-oxide obtained in Production Example 6, 125 mg of potassium phthalimide was added, followed by stirring at 130° C. for 3 hours. It was then cooled to room temperature, poured onto an ammonium chloride aqueous solution, and then extracted with ethyl acetate. The organic layer was washed with brine, dried over anhydrous magnesium sulfate, and then the solvent was evaporated. The resulting residue was purified by silica gel column chromatography, to give 204 mg of the title compound.

$^1$H-NMR(400 MHz, CDCl$_3$) d; 7.81–7.78(m,2H), 7.71–7.67(m,2H), 7.59(d,J=5,1H), 7.57(d,J=7,1H), 7.16(d,J=5,1H), 7.15(d,J=7,1H), 4.22–4.01(m,2H), 3.67–3.53(m,2H), 2.37(s,6H) 2.02–1.78(m,2H).

Example 3

9-(3-Aminopropyl)-7,8-dimethyl-3-thieno[1,4]benzothiazine-4-oxide

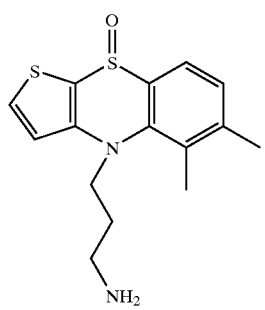

To a solution of 10 ml of methanol containing 200 mg of 7,8-dimethyl-9-(3-phthaliminopropyl)-3-thieno[1,4]benzothiazine-4-oxide obtained in the same manner as in Production Example 7, 0.22 ml of hydrazine monohydrate was added and heated under reflux for 1 hour. Methanol was evaporated, and water was added to the resulting residue, which was then extracted with a small amount of diethyl ether. The aqueous layer was extracted with dichloromethane, and the dichloromethane layer was washed with brine, dried over anhydrous magnesium sulfate and then the solvent was evaporated, to give 140 mg of the title compound.

$^1$H-NMR(400 MHz, CDCl$_3$) d; 7.60(d,J=5,1H), 7.59(d,J=8,1H), 7.19(d,J=5,1H), 7.16(d,J=7,1H), 4.26–4.05(m,2H), 2.63–2.49(m,2H), 2.40(s,3H), 2.39(s,3H), 1.70–1.58(m,2H).

Example 4

7,8-Dimethyl-9-[3-(2-thiophenyl)methylaminopropyl]-3-thieno[1,4]benzothiazine-4-oxide

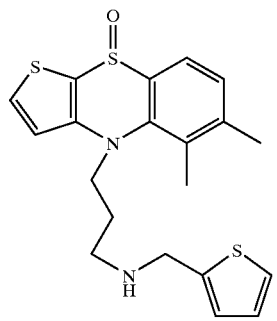

A solution of 10 ml of ethanol containing 100 mg of 9-(3-aminopropyl)-7,8-dimethyl-3-thieno[1,4]benzothiazine-4-oxide obtained in Example 3 and 40 mg of 2-formylthiophene was heated under reflux for 3 hours. Ethanol was evaporated. To a solution of 10 ml of methanol containing the resulting residue, 49 mg of sodium boron hydride was added under stirring at room temperature, followed by stirring at room temperature for 30 minutes. After water was added to the reaction solution, methanol was evaporated, and the resulting residue was extracted with ethyl acetate. The organic layer was washed with brine, dried over anhydrous magnesium sulfate and then the solvent was evaporated. The resulting residue was purified by silica gel column chromatography, to give 77 mg of the title compound.

$^1$H-NMR(400 MHz, CDCl$_3$) d; 7.59(d,J=5,1H), 7.59(d,J=8,1H), 7.19(d,J=5,1H), 7.17(dd,J=5,1,1H), 7.14(d,J=8,1H), 6.90(dd,J=5,3,1H), 6.81–6.79(m,1H), 4.25–4.16(m,2H), 3.79(dd,J=14,1,1H), 3.73(dd,J=14,1,1H), 2.72–2.50(m,2H), 2.41(s,3H), 2.38(S,3H), 1.72–1.62(m,2H).

The following compounds were obtained in the same manner as in Example 4.

TABLE 5

| Ex. No. | | ¹H-NMR (400 MHz) δ |
|---|---|---|
| 5 | 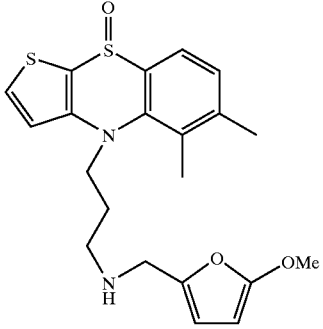 | CDCL₃<br>7.59(d, J=5, 1H), 7.39(d, J=8, 1H), 7.18(d, J=5, 1H), 7.15(d, J=8, 1H), 5.92(d, J=3, 1H), 4.99(d, J=3, 1H), 4.24–4.06(m, 2H), 3.79(s, 3H), 3.46(d, J=15, 1H), 3.42(d=15, 1H), 2.53–2.38(m, 2H), 2.39(s, 3H), 2.38(s, 3H), 1.72–1.56(m, 2H) |
| 6 | 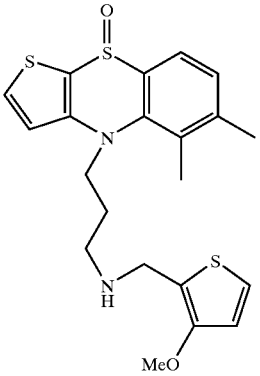 | CDCl₃<br>7.58(d, J=5, 1H), 7.58(d, J=8, 1H), 7.19(d, J=5, 1H), 7.14(d, J=8, 1H), 7.04(d, J=5, 1H), 6.78(d, J=5, 1H), 4.25–4.10(m, 2H), 3.77(s, 3H), 3.70(d, J=14, 1H), 3.64(d, J=14, 1H), 2.56–2.45(m, 2H), 2.40(s, 3H), 2.38(s, 3H), 1.74–1.56(m, 2H) |

Production Example 8

3,4-Dibromo-2-nitrothiophene

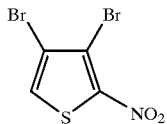

41.4 ml of fuming nitric acid was slowly added to 500 ml of acetic acid under ice-cooling, followed by stirring for 10 minutes, and a solution of 78 ml of acetic acid anhydride containing 50 g of 3,4-dibromothiophene was slowly added, followed by stirring at room temperature for 18 hours. Ice was added to the reaction solution, and the resulting crystals were collected by filtration, and washed with water and diethyl ether/n-hexane=1/5 successively, to give 40.2 g of the title compound.

¹H-NMR (400 MHz, CDCl₃) d; 7.61 (s,1H).

Production Example 9

9-H-1-Bromo-7,8-dimethyl-3-thieno[1,4]benzothiazine

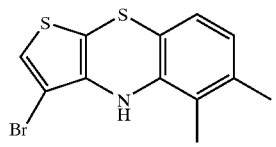

To a solution of 200 ml of N,N'-dimethylformamide containing 20. 6 g of 3,4-dibromo-2-nitrothiophene obtained in Production Example 8 and 11.0 g of 2-amino-3,4-dimethylthiophenol synthesized from 2,3-dimethylaniline by the method of a known literature, 19.8 g of potassium carbonate was added, followed by stirring at 100° C. for 3 hours. The reaction solution was poured onto an ammonium chloride aqueous solution and extracted with ethyl acetate. The organic layer was washed with brine, dried over anhydrous magnesium sulfate and then the solvent was evaporated. The resulting residue was purified by silica gel column chromatography, to give 6.38 g of the title compound.

¹H-NMR (400 MHz, CDCl₃) d; 7.06(s,1H), 6.75(d, J=8, 1H) 6.70(d,J=8,1H), 6.04(bs,1H), 2.26(s,3H), 2.16(s,3H).

Production Example 10

1-Bromo-7,8-dimethyl-9-(3-chloropropyl)-3-thieno[1,4]benzothiazine

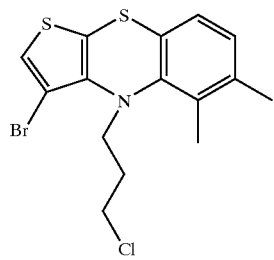

To a solution of 90 ml of N,N'-dimethylformamide containing 3.0 g of 9-H-1-bromo-7,8-dimethyl-3-thieno[1,4]benzothiazine obtained in Production Example 9, 460 mg of sodium hydride was added under stirring at room temperature, and after stirring for 30 minutes, 1.1 ml of 1-chloro-3-iodopropane was added thereto, followed by stirring at room temperature for 2 hours. Water was added to the reaction solution, which was then extracted with diethyl ether. The organic layer was washed with brine, dried over anhydrous magnesium sulfate and then the solvent was evaporated. The resulting residue was purified by silica gel column chromatography, to give 3.14 g of the title compound.

$^1$H-NMR(400 MHz, CDCl$_3$) d; 7.13(s,1H), 6.89(s,2H), 3.81–3.73(m,1H), 3.57–3.50(m,2H), 3.49–3.41(m,1H), 2.35 (s,3H), 2.27(s,3H), 2.16–1.96(m,2H).

Production Example 11

1-Bromo-9-(3chloropropyl)-7,8-dimethyl-3-thieno[1,4]benzothiazine-4-oxide

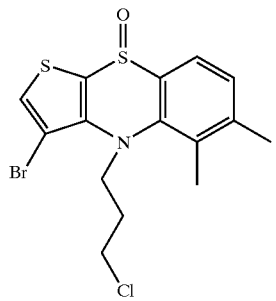

To a solution of 50 ml of dichloromethane containing 500 mg of 1-bromo-9-(3-chloropropyl)-7,8-dimethyl-3-thieno[1,4]benzothiazine obtained in Production Example 10, 216 mg of sodium hydrogen carbonate was added, followed by cooling to –50° C. 277 mg of m-chloroperbenzoic acid was slowly added thereto under stirring, and the temperature was raised from –50° C. to –20° C., it was stirred for 1 hour. The reaction solution was poured into water and extracted with dichloromethane. The organic layer was washed with brine, dried over anhydrous magnesium sulfate and then the solvent was evaporated. The resulting residue was purified by silica gel column chromatography, to give 470 mg of the title compound.

$^1$H-NMR(400 MHz, CDCl$_3$) d; 7.56(d,J=8,1H), 7.54(s, 1H), 7.19(d,J=8,1H), 4.72–3.62(m,1H), 4.03–3.93(m,1H), 3.48–3.36(m,2H), 2.48(s,3H), 2.40(s,3H), 1.98–1.90(m,2H).

Example 7

1-Bromo-7,8-dimethyl-9-[3-(α,α-dimethylbenzyl)aminopropyl]-3-thieno[1,4]benzothiazine-4-oxide

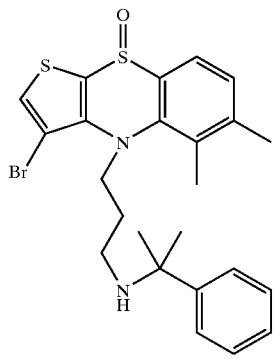

To a solution of 6 ml of toluene containing 120 mg of 1-bromo-9-(3-chloropropyl)-7,8-dimethyl-3-thieno[1,4]benzothiazine-4-oxide obtained in Production Example 11, 60 mg of cumylamine, 120 mg of tetra-n-butylammonium iodide and 61 mg of potassium carbonate were added. The resulting mixture was heated under reflux for 2 days. An ammonium chloride aqueous solution was added to the reaction solution, which was then extracted with ethyl acetate. The organic layer was washed with brine, dried over anhydrous magnesium sulfate and then the solvent was evaporated. The resulting residue was purified by silica gel column chromatography, to give 115 mg of the title compound.

$^1$H-NMR(400 MHz, CDCl$_3$) d; 7.54(d,J=8,1H), 7.50(s, 1H), 7.37–7.32(m,2H), 7.31–7.25(m,2H), 7.21–7.14(m,2H), 4.56–4.47(m,1H), 3.80–3.71(m,1H), 2.42(s,3H), 2.38(s,3H), 2.20–2.12(m,2H), 1.61–1.47(m,2H), 1.33(s,3H), 1.32(s,3H).

Production Example 12

1-Bromo-9-(3-phthaliminopropyl)-7,8-dimethyl-3-thieno[1,4]benzothiazine-4-oxide

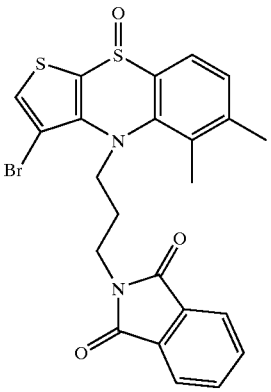

To a solution of 15 ml of N,N'-dimethylformamide containing 470 mg of 1-bromo-9-(3-chloropropyl)-7,8-dimethyl-3-thieno[1,4]benzothiazine-4-oxide obtained in the same manner as in Production Example 11, 237 mg of potassium phthalimide was added, followed by stirring at 130° C. for 1 hour. It was then cooled to room temperature and then poured onto an ammonium chloride aqueous solution, which was extracted with ethyl acetate. The organic layer was washed with brine, dried over anhydrous magnesium sulfate and then the solvent was evaporated. The resulting crystals were washed with diethyl ether, to give 578 mg of the title compound.

$^1$H-NMR(400 MHz, CDCl$_3$) d; 7.82–7.78(m,2H), 7.71–7.67(m,2H), 7.57(d,J=8,1H), 7.49(s,1H), 7.16(d,J=8, 1H), 4.66–4.57(m,1 H) 3.81–3.72(m,1H), 3.65–3.55(m,2H), 2.42(s,3H), 2.38(s,3H), 1.92–1.81(m,2H).

Production Example 13

9-(3-Aminopropyl)-1-bromo-7,8-dimethyl-3-thieno[1,4]benzothiazine-4-oxide

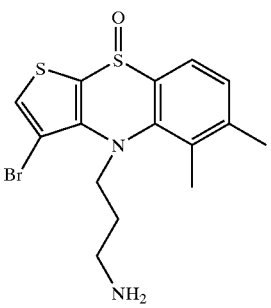

To a solution of 15 ml of methanol containing 550 mg of 1-bromo-7,8-dimethyl-9-(3-phthaliminopropyl)-3-thieno[1,4]benzothiazine-4-oxide obtained in Production Example 12, 0.5 ml of hydrazine monohydrate was added, and the mixture was heated under reflux for 2 hours. Methanol was evaporated, and water was added to the residue, which was then extracted with a small amount of diethyl ether. The aqueous layer was extracted with dichloromethane, and the dichloromethane layer was washed with brine, dried over anhydrous magnesium sulfate and then the solvent was evaporated, to give 313 mg of the title compound.

$^1$H-NMR(400 MHz, CDCl$_3$) d; 7.54(d,J=8,1H), 7.52(s, 1H), 7.18(d,J=8,1H), 4.62–4.52(m,1H), 3.83–3.73(m,1H), 2.58–2.53(m,2H), 2.43(s,3H), 2.39(s,3H), 1.65–1.55(m,2H).

Example 8

9-(3-benzylaminopropyl)-7,8-dimethyl-3-thieno[1,4]benzothiazine-4-oxide

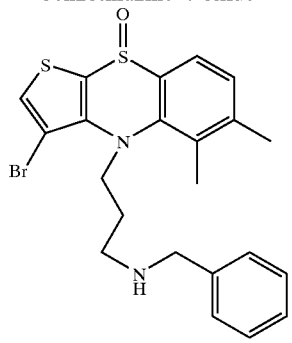

A solution of 8 ml of ethanol containing 80 mg of 9-(3-aminopropyl)-1-bromo-7,8-dimethyl-3-thieno[1,4]benzothiazine-4-oxide obtained in Production Example 13 and 26 mg of benzaldehyde was heated under reflux for 2 hours. Ethanol was evaporated, and to a solution of 8 ml of methanol solution containing the resulting residue, 31 mg of sodium boron hydride was added under stirring at room temperature, followed by stirring at room temperature for 20 minutes. After water was added to the reaction solution, methanol was evaporated, and the resulting residue was extracted with ethyl acetate. The organic layer was washed with brine, dried over anhydrous magnesium sulfate and then the solvent was evaporated. The resulting residue was purified by silica gel column chromatography, to give 70 mg of the title compound.

$^1$H-NMR(400 MHz, CDCl$_3$) d; 7.54(d,J=8,1H), 7.52(s, 1H), 7.30–7.15(m,6H), 4.63–4.55(m,1H), 3.85–3.76(m,1H), 3.64(bs,2H), 2.52–2.47(m,2H), 2.43(s,3H), 2.38(s,3H), 1.76–1.61(m,2H).

The following compounds were obtained in the same manner as in Example 8.

TABLE 6

| Ex. No. | Structure | $^1$H-NMR (400 MHz) δ |
|---|---|---|
| 09 | (structure shown) | CDCl$_3$<br>7.54(d, J=8, 1H), 7.51(s, 1H), 7.16(d, J=8, 1H), 7.03(d, J=5, 1H), 6.77(d, J=5, 1H), 4.62–4.53(m, 1H), 3.87–3.77(m, 1H), 3.77(s, 3H), 3.70(s, 2H), 2.53–2.46(m, 2H), 2.45(s, 3H), 2.39(s, 3H), 1.70–1.50(m, 2H) |
| 10 | (structure shown) | CDCl$_3$<br>7.55(d, J=8, 1H), 7.54(s, 1H), 7.19(d, J=8, 1H), 6.98–6.91(m, 1H), 6.68–6.61(m, 2H), 4.66–4.57(m, 1H), 3.85(s, 2H), 3.79–3.70(m, 1H), 2.48(t, J=7, 2H), 2.44(s, 3H), 2.40(s, 3H), 1.85–1.65(m, 2H) |

Production Example 14

9(3-Chloropropyl)-1-formyl-7,8-dimethyl-3-thieno[1,4]benzothiazine

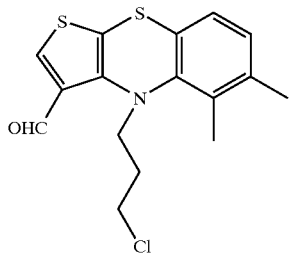

To a solution of 25 ml of tetrahydrofuran containing 500 mg of 9-(3-chloropropyl)-1-bromo-7,8-dimethyl-3-thieno[1,4]benzothiazine-4-oxide obtained in the same manner as in Production Example 11, which was cooled to −78° C. under a nitrogen stream, 0.86 ml of t-butyllithium (1.64 M n-pentane solution) was added. After stirring at −78° C. for 10 minutes, 0.12 ml of N,N'-dimethylformamide was added thereto and then the mixture was stirred for 30 minutes. Water was added to the reaction solution, which was then extracted with ethyl acetate. The organic layer was washed with brine a saturated ammonium chloride aqueous solution and brine successively, dried over anhydrous magnesium sulfate and then the solvent was evaporated. The resulting residue was purified by silica gel column chromatography, to give 140 mg of the title compound.

$^1$H-NMR(400 MHz, CDCl$_3$) d; 9.88(s,1H), 7.96(s,1H), 6.88(s,2H), 3.81–3.73(m,1H), 3.62–3.46(m,3H), 2.32(s,3H), 2.26(s,3H), 2.12–1.96(m,2H).

Production Example 15

9-(3-Chloropropyl)-1-formyl-7,8-dimethyl-3-thieno[1,4]benzothiazine-4-oxide

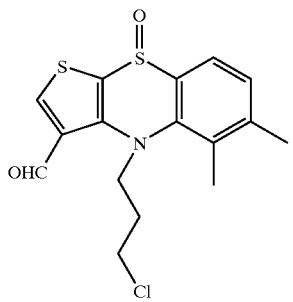

To a solution of 14 ml of dichloromethane containing 140 mg of 9-(3-chloropropyl)-1-formyl-7,8-dimethyl-3-thieno[1,4]benzothiazine obtained in Production Example 14, 70 mg of sodium hydrogen carbonate was added, followed by cooling to −60° C. 89 mg of m-chloroperbenzoic acid was slowly added thereto under stirring, and while the temperature was raised from −60° C. to −10° C., it was stirred for 1 hour. The reaction solution was poured into water and extracted with dichloromethane. The organic layer was washed with brine, dried over anhydrous magnesium sulfate and then the solvent was evaporated. The resulting residue was purified by silica gel column chromatography, to give 136 mg of the title compound.

$^1$H-NMR(400 MHz, CDCl$_3$) d; 10.06(s,1H), 8.38(s,1H) 7.57(d,J=8,1H), 7.21(d,J=8,1H), 4.46–4.37(m,1H), 4.23–4.13(m,3H), 3.36(t,J=6,2H), 2.49(s,3H), 2.41(s,3H), 1.91–1.82(m,2H).

Production Example 16

9-(3-Chloropropyl)-1hydroxymethyl1-7,8-dimethyl-3-thieno[1,4]benzothiazine-4-oxide

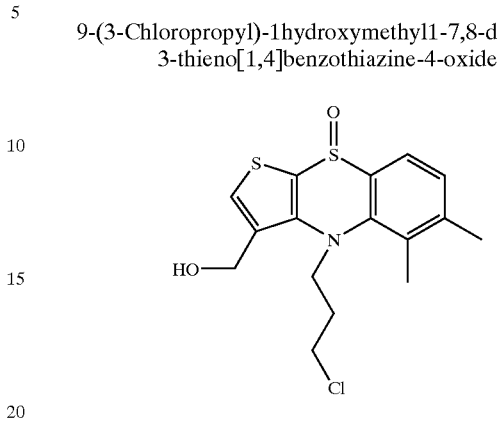

To a solution of 13 ml of methanol and 5 ml of dichloromethane containing 135 mg of 9-(3-chloropropyl)-1-formyl-7,8-dimethyl-3-thieno[1,4]benzothiazine-4-oxide obtained in Production Example 15, 44 mg of sodium boron hydride was added under stirring at room temperature, followed by stirring at room temperature for 30 minutes. After water was added thereto, methanol and dichloromethane were evaporated, and the resulting residue was extracted with ethyl aceate. The organic layer was washed with brine, dried over anhydrous magnesium sulfate and then the solvent was evaporated. The resulting residue was purified by silica gel column chromatography, to give 140 mg of the title compound.

$^1$H-NMR(400 MHz, CDCl$_3$) d; 7.55 (d,J=8,1H), 7.55 (s,1H), 7.17(d,J=8,1H), 4.90–4.82(m,2H), 4.31–4.21(m, 1H), 4.04–3.94(m,1H), 3.49–3.36(m,2H), 2.43(s,3H), 2.38 (s,3H), 2.00–1.88(m,2H).

Example 11

9-(3-benzylaminopropyl)-1-hydroxymethyl-7,8dimethyl-3-thieno[1,4]benzothiazine-4-oxide

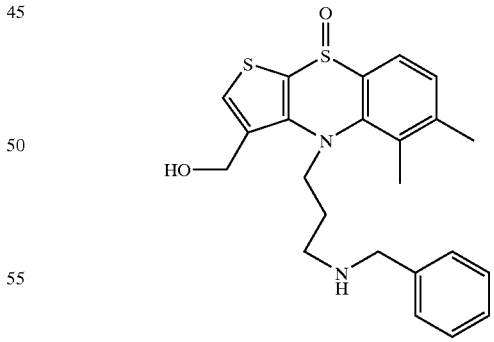

To a solution of 7 ml of xylene containing 140 mg of 9-(3-chloropropyl)-1-hydroxymethyl-7,8-dimethyl-3-thieno[1,4]benzothiazine-4-oxide obtained in Production Example 16, 0.43 ml of benzylamine was added and heated under reflux for 3 hours. An ammonium chloride aqueous solution was added to the reaction solution, which was then extracted with ethyl acetate. The organic layer was washed with brine, dried over anhydrous magnesium sulfate and then the solvent was evaporated. The resulting residue was purified by silica gel column chromatography, to give 69 mg of the title compound.

$^1$H-NMR(400 MHz, CDCl$_3$) d; 7.57(s,1H), 7.52(d,J=8, 1H), 7.33–7.28(m,5H), 7.16(d,J=8,1H), 4.79(d,J=12,1H), 4.70(d,J=12,1H) 4.89–4.49(m,1H), 3.86–3.78(m,1H), 3.69 (s,2H), 2.59–2.45(m,2H), 2.41(s,3H), 2.38(s,3H), 1.93–1.83 (m,1H), 1.76–1.65(m,1H).

Production Example 17

1-Bromo-9-(3-chloropropyl)-2-formyl-7,8-(dimethyl-3-thieno[1,4]benzothiazine

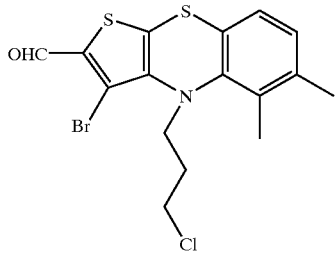

To a solution of 50 ml of tetrahydrofuran containing 1.0 g of 1-bromo-9-(3-chloropropyl)-7,8-dimethyl-3-thieno[1,4]benzothiazine-4-oxide obtained in the same manner as in Production Example 11, which was cooled to −78° C. under a nitrogen stream, 0.92 ml of t-butyllithium (1.64 M n-pentane solution) was added. After stirring at −78° C. for 10 minutes, 0.24 ml of N,N'-dimethylformamide was added thereto, and the mixture was stirred with raising the temperature to room temperature over 2 hours. Water was added to the reaction solution, which was then extracted with ethyl acetate. The organic layer was washed with a saturated ammonium chloride aqueous solution and brine successively, dried over anhydrous magnesium sulfate and then the solvent was evaporated. The resulting residue was purified by silica gel column chromatography, to give 319 mg of the title compound.

$^1$H-NMR(400 MHz, CDCl$_3$) d; 9.87(s,1H), 6.93(d,J=8, 1H), 6.89 (d,J=8,1H), 3.83–3.74(m,1H), 3.55–3.43(m,3H), 2.35(s,3H) 2.27(s,3H), 2.12–1.96(m,2H).

Production Example 18

1-Bromo-9-(3-chloropropyl )-2-formyl-7,8-dimethyl-3-thieno[1,4]benzothiazine-4-oxide

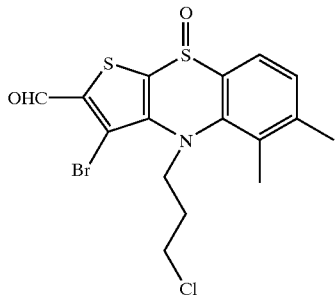

To a solution of 32 ml of dichloromethane containing 319 mg of 1-bromo-9-(3-chloropropyl)-2-formyl-7,8-dimethyl-3-thieno[1,4]benzothiazine obtained in Production Example 17, 129 mg of sodium hydrogen carbonate was added, followed by cooling to −78° C. 165 mg of m-chloroperbenzoic acid was slowly added thereto under stirring, and while the temperature was raised from −78° C. to −10° C., it was stirred for 1 hour. The reaction solution was poured into water and extracted with dichloromethane. The organic layer was washed with brine, dried over anhydrous magnesium sulfate and then the solvent was evaporated. The resulting residue was purified by silica gel column chromatography, to give 319 mg of the title compound.

$^1$H-NMR(400 MHz, CDCl$_3$) d; 10.12(s,1H), 7.57(d,J=8, 1H), 7.23.(d,J=8,1H), 4.68–4.59(m,1H), 4.07–3.98(m,1H), 3.48–3.36(m,2H), 2.49(s,3H), 2.42(s,3H), 1.99–1.92(m,2H).

Production Example 19

1-Bromo-9-(3-chloropropyl)-2-hydroxymethyl7,8-dimethyl-3-thieno[1,4]benzothiazine-4-oxide

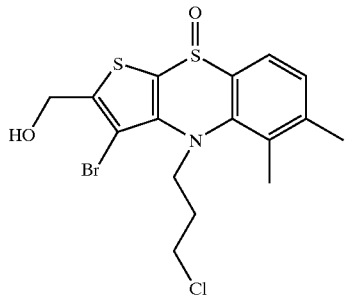

To a solution of 16 ml of methanol and 8 ml of dichloromethane containing 319 mg of 1-bromo-9-(3-chloropropyl)-2-formyl-7,8-dimethyl-3-thieno[1,4]benzothiazine-4-oxide obtained in Production Example 18, 56 mg of sodium boron hydride was added under stirring at room temperature, followed by stirring at room temperature for 30 minutes. After water was added thereto, methanol and dichloromethane were evaporated, and the resulting residue was extracted with ethyl acetate. The organic layer was washed with brine, dried over anhydrous magnesium sulfate and then the solvent was evaporated. The resulting residue was purified by silica gel column chromatography, to give 300 mg of the title compound.

$^1$H-NMR(400 MHz, CDCl$_3$) d; 7.55(d,J=8,1H), 7.18(d,J= 8,1H), 4.94–4.80(m,2H), 4.68–4.59(m,1H), 4.01–3.92(m, 1H), 3.47–3.35(m,2H), 2.48(s,3H), 2.40(s,3H), 1.97–1.89 (m,2H).

Example 12

1-Bromo-9-(3-benzylaminopropyl)-2-hydroxymethyl-7,8-dimethyl-3-thieno[ 1,4]benzothiazine-4-oxide

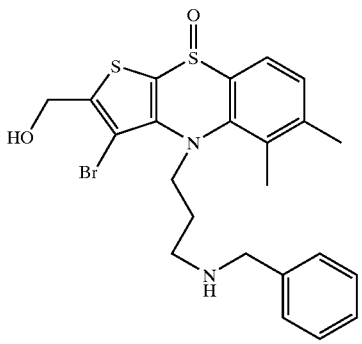

To a solution of 15 ml of xylene containing 300 mg of 1-bromo-9-(3-chloropropyl)-2-hydroxymethyl-7,8-dimethyl-3-thieno[1,4]benzothiazine-4-oxide obtained in Production Example 19, 0.75 ml of benzylamine was added and heated under reflux for 3 hours. An ammonium chloride aqueous solution was added to the reaction solution, which was then extracted with ethyl acetate. The organic layer was washed with brine, dried over anhydrous magnesium sulfate and then the solvent was evaporated. The resulting residue was purified by silica gel column chromatography, to give 290 mg of the title compound.

$^1$H-NMR(400 MHz, CDCl$_3$) d; 7.53(d,J=9,1H), 7.36–7.14(m,6H), 4.84(d,J=15,1H), 4.75(d,J=15,1H), 4.61–4.52(m,1H), 3.87(s,1H), 3.83–3.74(m,1H), 3.62(s,2H), 2.48(t,J=7,2H), 2.43(s,3H), 2.38(s,3H), 1.75–1.60(m,2H).

Production Example 20

2,3-Dimethylphenyl-3-nitro-2-pyridinylsulfide

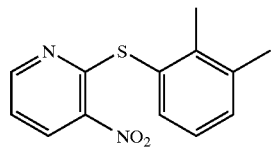

2.4 g of 2-chloro-3-nitropyridine and 2.1 g of 2,3-dimethylthiophenol were dissolved in 20 ml of N,N-dimethylformamide and reacted at an external temperature of 70° C. for 30 minutes. 5 g of potassium carbonate was added thereto, and the reaction was further continued at the same temperature for 90 minutes. Water was then added thereto, and it was extracted with ethyl acetate. After washing with water and brine successively, it was dried over anhydrous sodium sulfate. After concentration, it was washed with ether to give 2 g of the title compound.

$^1$H-NMR(400 MHz, CDCl$_3$) d; 9.37(s,1H), 8.34(d,J=6, 1H) 7.43(d,J=8,1H), 7.37(d,J=8,1H), 7.24(t,J=8,1H), 6.57(d, J=6,1H), 2.39(s,3H), 2.32(s,3H).

Production Example 21

1,2-Dimethyl-6-azaphenothiazine

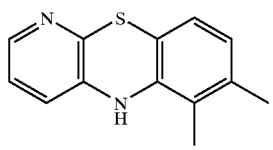

2 g of 2,3-dimethylphenyl-3-nitro-2-pyridinylsulfide obtained in Production Example 20 was reacted under reflux in 100 ml of cumene in the presence of 9.3 g of triethyl phosphite for 4.5 hours. The reaction solution was allowed to cool to room temperature, and purified by silica gel column chromatography, to give 1.0 g of the title compound.

$^1$H-NMR(400 MHz, CDCl$_3$) d; 7.91(dd,J=5,2,1H), 6.85 (dd,J=8,5,1H), 6.75(d,J=,1H), 6.72(dd,J=8,2,1H), 6.67(d,J= 8,1H), 5.65(brs,1H), 2.21(s,3H), 2.11(s,3H).

The following compounds were synthesized by applying the procedures in Production Example 5, Production Example 6, Production Example 7 and Example 3 to 1,2-dimethyl-6-azaphenothiazine obtained in Production Example 21.

TABLE 7

| Ex. No. | | $^1$H-NMR (400 MHz) δ |
|---|---|---|
| 13 | (structure) | CDCl$_3$<br>8.42(dd, J=4, 2, 1H), 7.88(dd, J=8, 2, 1H), 7.66(d, J=8, 1H), 7.46(dd, J=8, 4, 1H), 7.19(d, J=8, 1H), 4.31(m, 1H), 4.05(m, 1H), 2.61(brs, 2H), 2.41(s, 3H), 2.40(s, 3H), 1.70–1.60(m, 2H) |
| 14 | (structure) | CDCl$_3$<br>8.43(dd, J=4, 2, 1H), 7.88(dd, J=8, 2, 1H), 7.67(d, J=8, 1H), 7.47(dd, J=8, 4, 1H), 7.19(d, J=8, 1H), 4.47(m, 1H), 4.05(m, 1H), 2.99(m, 1H), 2.73(m, 1H), 2.41(s, 3H), 2.40(s, 3H), 2.56–2.49(m, 2H), 2.33(s, 3H), 2.26(s, 3H), 1.41–1.31(m, 2H) |

The following compounds were synthesized by applying the procedures in Example 4 to the compound obtained in Example 13, or by applying the procedures in Production Example 5, Production Example 6 and Example 1 to 1,2-dimethyl-6-azaphenothiazine obtained in Production Example 21.

TABLE 8

| Ex. No. | | $^1$H-NMR (400 MHz) δ |
|---|---|---|
| 15 | 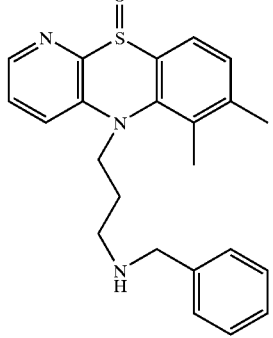 | CDCl$_3$<br>8.41(dd, J=4, 2, 1H), 7.85(dd, J=8, 2, 1H), 7.65(d, J=8, 1H), 7.43(dd, J=8, 4, 1H), 7.40–7.16(m, 6H), 4.30(m, 1H), 4.09(m, 1H), 3.61(s, 2H), 2.53(t, J=7, 2H), 2.40(s, 3H), 2.39(s, 3H), 1.76–1.65(m, 2H) |
| 16 | 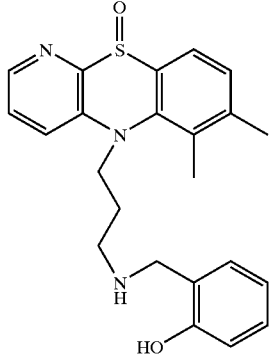 | CDCl$_3$<br>8.43(dd, J=4, 2, 1H), 7.86(dd, J=8, 2, 1H), 7.65(d, J=8, 1H), 7.47(dd, J=8, 4, 1H), 7.20(dd, J=8, 1H), 7.17–6.70(m, 4H), 4.33(m, 1H), 4.03(m, 1H), 3.84(d, J=14, 1H), 3.80(d, J=14, 1H), 2.57–2.52(m, 2H), 2.41(5, 6H), 1.80–1.70(m, 2H) |
| 17 | 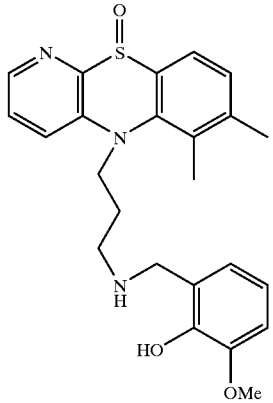 | CDCl$_3$<br>8.42(dd, J=4, 2, 1H), 7.87(dd, J=8, 2, 1H), 7.65(d, J=8, 1H), 7.46(dd, J=8, 4, 1H), 7.19(d, J=8, 1H), 6.82–6.52(m, 3H), 4.34(m, 1H), 4.01(m, 1H), 3.88(d, J=14, 1H), 3.87(s, 3H), 3.79(d, J=14, 1H), 2.60–2.38(m, 2H), 2.39(s, 6H), 1.81–1.71(m, 2H) |

TABLE 8-continued
| Ex. No. | | $^1$H-NMR (400 MHz) δ |
|---|---|---|
| 18 | 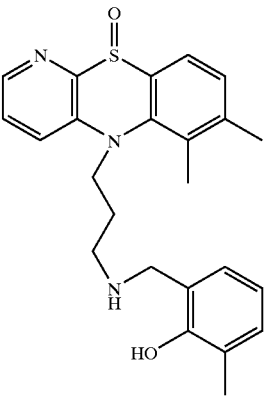 | CDCl$_3$<br>8.43(dd, J=4, 1, 1H), 7.86(dd, J=8, 1H), 7.66(d, J=8, 1H), 7.46(dd, J=g, 4, 1H), 7.20(d, J=8, 1H), 7.02(d, J=8, 1H), 6.75(d, J=g, 1H), 6.65(t, J=8, 1H), 4.34(m, 1H), 4.04(m, 1H), 3.78(s, 2H), 2.54(t, J=7, 3H), 2.42(s, 3H), 2.41(s, 3H), 2.22(s, 3H), 1.80–1.70(m, 2H) |
| 19 | 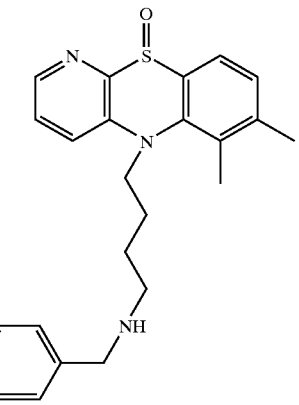 | CDCl$_3$<br>8.42(dd, J=4, 2, 1H), 7.83(dd, J=8, 2, 1H), 7.65(d, J=8, 1H), 7.44(dd, J=8, 4, 1H), 7.31–7.21(m, 5H), 7.18(d, J=8, 1H), 4.21(m, 1H), 3.93(m, 1H), 3.68(s, 2H), 2.49(t, J=7, 2H), 2.38(s, 3H), 2.37(s, 3H), 1.62–1.55(m, 2H), 1.49–1.37(m, 2H) |
| 20 | 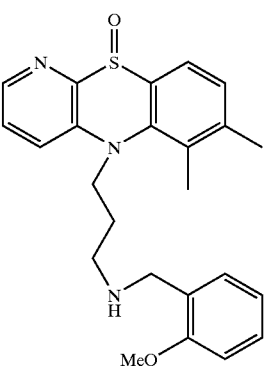 | CDCl$_3$<br>8.41(dd, J=4, 2, 1H), 7.86(dd, J=8, 2, 1H), 7.64(d, J=8, 1H), 7.43(dd, J=8, 4, 1H), 7.24–6.80(m, 5H), 4.29(m, 1H), 4.05(m, 1H), 3.77(s, 3H), 3.66(s, 2H), 2.56–2.46(m, 2H), 2.39(s, 3H), 2.38(s, 3H) 1.80–1.70(m, 2H) |
| 21 | 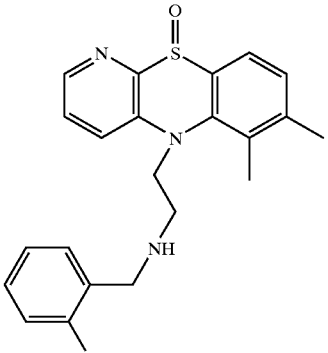 | CDCl$_3$<br>8.45(d, J=4, 2, 1H), 7.89(dd, J=8, 2, 1H), 7.68(d, J=8, 1H), 7.50(dd, J=8, 4, 1H), 7.24(d, J=8, 1H), 7.12–6.65(m, 4H), 4.44(m, 1H), 4.18(m, 1H), 3.78(d, J=14, 1H), 3.53(d, J=14, 1H), 2.81(m, 1H), 2.59(m, 1H), 2.43(5, 3H), 2.40(s, 3H), |

TABLE 9
| Ex. No. | | ¹H-NMR (400 MHz) δ |
|---|---|---|
| 22 | 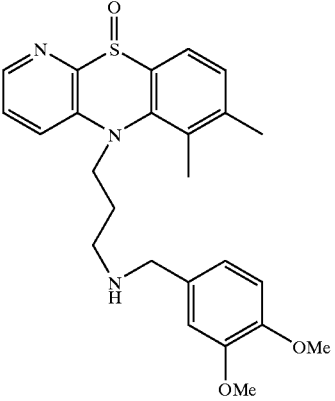 | CDCl₃<br>8.42(dd, J=4, 1, 3H), 7.85(dd, J=8, 1, 1H), 7.66(d, J=8, 1H), 7.44(dd, J=8, 4, 1H), 7.19(d, J=8, 1H), 6.80–6.70(m, 3H), 4.30(m, 1H), 4.10(m, 1H), 3.86(s, 6H), 3.57(s, 2H), 2.56–2.47(m, 2H), 2.40(s, 3H), 2.39(s, 3H), 1.78–1.64(m, 2H) |
| 23 | 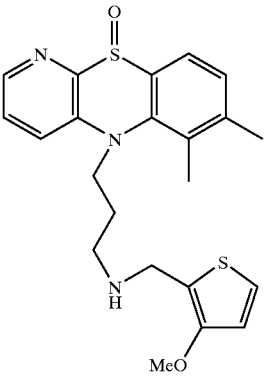 | CDCl₃<br>8.42(dd, J=4, 1H), 7.88(dd, J=8, 1H), 7.63(d, J=8, 1H), 7.46(dd, J=8, 4, 1H), 7.19(d, J=8, 1H), 7.08(d, J=5, 1H), 6.78(d, J=5, 1H), 4.33(m, 1H), 4.11(m, 1H), 3.77(s, 3H), 3.76(s, 2H), 2.56(t, J=7, 2H), 2.41(s, 3H), 2.40(s, 3H), 1.80–1.65(m, 2H) |
| 24 | 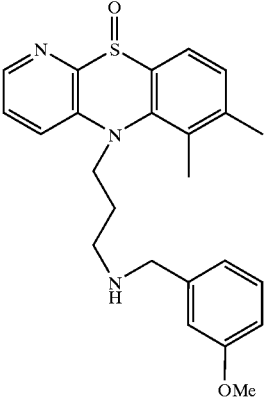 | CDCl₃<br>8.42(dd, J=4, 2, 1H), 7.85(dd, J=8, 2, 1H), 7.65(d, J=8, 1H), 7.44(dd, J=8, 4, 1H), 7.23–7.17(m, 2H), 6.79–6.74(m, 3H), 4.31(m, 1H), 4.11(m, 1H), 3.79(s, 3H), 3.60(s, 2H), 2.53(t, J=7, 2H), 2.40(s, 3H), 2.39(s, 3H), 1.78–1.64(m, 2H) |
| 25 | 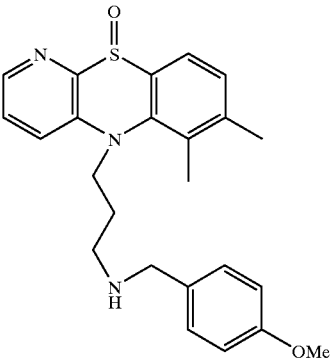 | CDCl₃<br>8.42(dd, J=4, 1, 1H), 7.85(dd, J=8, 1H), 7.65(d, J=8, 1H), 7.44(dd, J=8, 4, 1H), 7.19(d, J=8, 1H), 7.12(d, J=8, 1H), 6.81(d, J=8, 1H), 4.30(m, 1H), 4.09(m, 1H), 3.79(s, 3H), 3.56(s, 2H), 2.53(t, J=7, 2H), 2.39(s, 6H), 1.77–1.64(m, 2H) |

TABLE 9-continued
| Ex. No. | | $^1$H-NMR (400 MHz) δ |
|---|---|---|
| 26 | 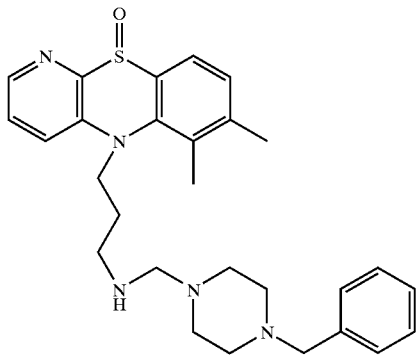 | CDCl$_3$<br>8.42(dd, J=4, 1, 1H), 7.86(dd, J=8, 1, 1H), 7.65(d, J=8, 1H), 7.44(dd, J=8, 4, 1H), 7.32–7.20(m, 5H), 7.18(d, J=8, 1H), 4.22(m, 1H), 4.09(m, 1H), 3.45(s, 2H), 2.40(s, 3H), 2.39(s, 3H), 2.45–2.12(m, 10H), 1.74–1.60(m, 2H) |
| 27 | 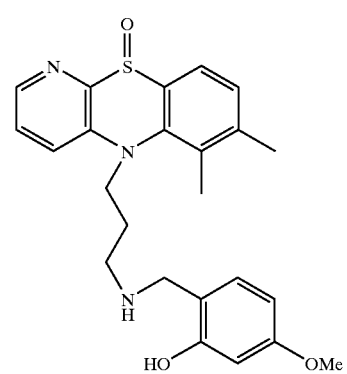 | CDCl$_3$<br>8.42(dd, J=4, 1, 1H), 7.86(dd, J=8, 1, 1H), 7.65(d, J=8, 1H), 7.47(dd, J=8, 4, 1H), 7.20(d, J=8, 1H), 6.80(d, J=8, 1H), 6.39(d, J=2, 1H), 6.31(dd, J=8, 2, 1H), 4.33(m, 1H), 4.03(m, 1H), 3.76(s, 3H), 2.54(t, J=7, 2H), 2.41(s, 6H), 1.82–1.66(m, 2H) |
| 28 | 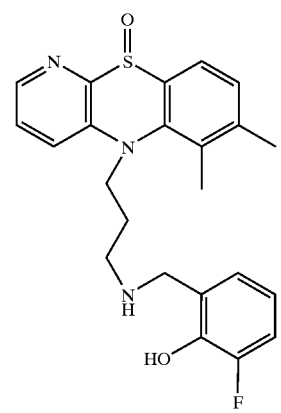 | CDCl$_3$<br>8.42(dd, J=4, 1, 1H), 7.89(J=8, 3, 1H), 7.64(d, J=8, 1H), 7.48(dd, J=8, 4, 1H), 7.20(d, J=8, 3H), 6.95(m, 1H), 6.72–6.60(m, 2H), 4.37(m, 1H), 4.03(m, 1H), 3.87(d, J=14, 1H), 3.82(d, J=14, 1H), 2.60–2.52(m, 2H), 2.41(s, 6H), 1.86–1.70(m, 2H) |

TABLE 10

| Ex. No. | | $^1$H-NMR (400 MHz) δ |
|---|---|---|
| 29 | (structure) | CDCl$_3$<br>8.42(dd, J=4, 1, 1H), 7.86(dd, J=8, 1, 1H), 7.65(d, J=8, 1H), 7.42(dd, J=8, 4, 1H), 7.24–6.95(m, 5H), 4.31(m, 1H), 4.10(m, 1H), 3.68(s, 2H), 2,53(t, J=7, 2H), 2.39(s, 3H), 2.38(s, 3H), 1.75–1.65(m, 2H) |
| 30 | (structure) | CDCl$_3$<br>8.43(d, J=4, 1H), 7.86(d, J=8, 1H), 7.65(d, J=8, 1H), 7.47(dd, J=8, 4, 1H), 7.20(d, J=8, 1H), 6.76–6.68(m, 2H), 6.50(d, J=2, 1H), 4.33(m, 1H), 4.04(m, 1H), 3.78(s, 2H), 3.71(s, 3H), 2.55(t, J=7, 2H), 2.41(s, 6H), 1.82–1.68(m, 2H) |
| 31 | (structure) | CDCl$_3$<br>8.42(dd, J=4, 1, 1H), 7.86(dd, J=8, 1, 1H), 7.65(d, J=8, 1H), 7.45(dd, J=8, 4, 1H), 7.31(d, J=2, 1H), 7.20(d, J=8, 1H), 7.18–7.12(m, 2H), 4.32(m, 1H), 4.12(m, 1H), 3.66(s, 2H), 2.52(t, J=7, 1H), 2.40(s, 3H), 2.39(s, 3H), 1.76–1.64(m, 2H) |
| 32 | (structure) | CDCl$_3$<br>8.42(dd, J=4, 1H), 7.86(dd, J=8, 1, 1H), 7.62(d, J=8, 1H), 7.44(dd, J=8, 4, 1H), 7.20–7.10(m, 2H), 6.67–6.52(m, 3H), 4.16(m, 1H), 4.06(m, 1H), 3.62(s, 2H), 2.90(s, 6H), 2.60(t, J=7, 2H), 2.39(s, 6H), 1.85–1.65(m, 2H) |

TABLE 10-continued

| Ex. No. | | $^1$H-NMR (400 MHz) δ |
|---|---|---|
| 33 | 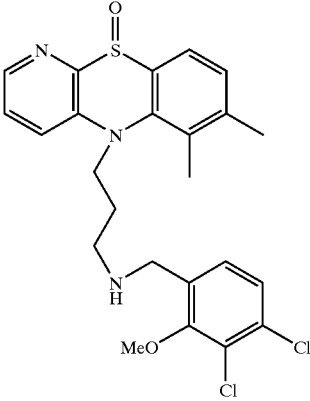 | CDCl$_3$<br>8.42(dd, J=4, 1, 1H), 7.85(dd, J=8, 1, 1H), 7.64(d, J=8, 1H), 7.45(dd, J=8, 4, 1H), 7.19(d, J=8, 1H), 7.14(d. J=8, 1H), 7.03(d, J=8, 1H), 4.30(m, 1H), 4.10(m, 1H), 3.78(s, 3H), 3.61(s, 2H), 2.49(t, J=7, 2H), 2.39(s, 6H), 1.76–1.65(m, 2H) |
| 34 | 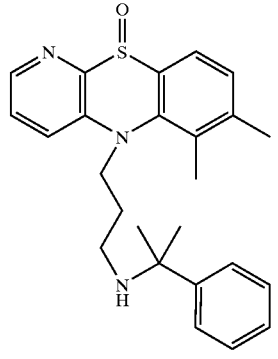 | CDCl$_3$<br>8.40(dd, J=1, 4, 1H), 7.82(dd, J=1, 8, 1H), 7.64(d, J=8, 1H), 7.42(dd, J=6, 8, 1H), 7.36–7.46(m, 6H), 4.28–4.18(m, 1H), 4.08–3.98(m, 1H), 2.38(s, 6H), 2.27–2.12(m, 2H), 1.64–1.50(m, 2H), 1.30(s, 3H), 1.28(s, 3H) |
| 35 | 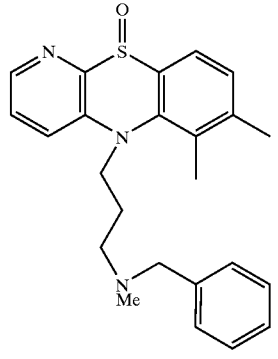 | CDCl$_3$<br>8.41(dd, J=4, 1, 1H), 7.85(dd, J=8, 1, 1H), 7.65(d, J=8, 1H), 7.43(dd, J=8, 1H), 7.32–7.16(m, 6H), 4.28(m, 1H), 4.09(m, 1H), 3.34(d, J=14, 1H), 3.30(d, J=14, 1H), 2.40(s, 3H), 2.39(s, 3H), 2.36(m, 1H), 2.27(m, 1H), 1.77–1.67(m, 2H) |

Production Example 22

4-Chloro-3-nitropyridine

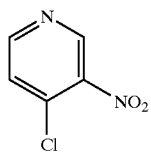

5 g of 4-hydroxy-3-nitropyridine and 15.5 g of phosphorous pentachloride were added to 100 ml of dichloroethane and reacted under reflux for 90 minutes. When it was poured onto ice to separate an organic phase and allowed to stand at room temperature for a while, crystals were precipitated. They were collected by filtration and washed with hexane, to give 4.3 g of the title compound.

$^1$H-NMR(400 MHz, DMSO-d$_6$) d; 9.25(s,1H), 8.83(d,J=5,1H), 7.93(d,J=5,1H).

Production Example 23

2-Amino-3,4-dimethylphenyl-3-nitro-4-pyridinylsulfide

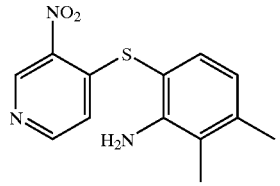

2.6 g of 4-chloro-3-nitropyridine obtained in Production Example 22, 5.1 g of 2-amino-3,4-dimethylthiophenol and 26 g of potassium carbonate were added to 100 ml of N,N-dimethylformamide and reacted at an external temperature of 80° C. for 1 hour. Water was then added thereto, and it was extracted with ethyl acetate. Then, it was washed with water and brine successively, and dried over anhydrous sodium sulfate. After concentration, the resulting residue was purified by silica gel chromatography, to give 4.2 g of the title compound.

$^1$H-NMR(400 MHz, CDCl$_3$) d; 9.37(s,1H), 8.38(d,J=6, 1H), 7.19(d,J=8,1H), 6.75(d,J=6,1H), 6.72(d,J=8,1H), 4.25 (brs,2H), 2.36(s,3H), 2.15(s,3H).

Production Example 24

2-Bromo-3,4-dimethylphenyl-3-nitro-4-pyridinylsulfide

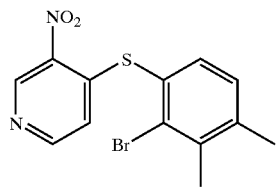

1 g of 2-amino-3,4-dimethylphenyl-3-nitro-4-pyridinylsulfide obtained in Production Example 23 was added to 4 ml of 48% aqueous HBr, and 4 ml of water was further added thereto. 0.26 g of sodium nitrite was added thereto at from 0 to 5° C. to react at the same temperature for 30 minutes. A solution obtained by dissolving 0.63 g of copper(I) bromide in 4 ml of 48% aqueous HBr was added thereto and reacted at an external temperature of 120° C. for 1 hour. After adding ice-cold water thereto, it was basified with a sodium hydroxide aqueous solution and extracted with ethyl acetate. It was washed with water and brine successively, and dried over anhydrous sodium sulfate. After concentration, 0.75 g of the title compound was obtained.

$^1$H-NMR(400 MHz, CDCl$_3$) d; 9.20(brs,1H), 8.40(brs, 1H) 7.47(d,J=8,1H), 7.25(d,J=8,1H), 6.63(brs,1H), 2.52(s, 3H), 2.44(s,3H).

Production Example 25

2-Bromo-3,4-dimethylphenyl-3-amino-4-pyridinylsulfide

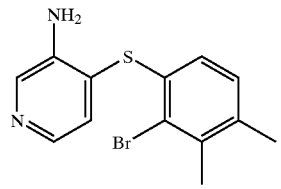

0.75 g of 2-bromo-3,4-dimethylphenyl-3-nitro-4-pyridinylsulfide obtained in Production Example 24 and 1.33 g of iron powder were added to a mixed solvent of 8 ml of ethanol and 2 ml of water. 1 ml of concentrated hydrochloric acid was further added thereto, and it was reacted under reflux for 1 hour. After the insoluble matters were filtered off, it was concentrated, a sodium hydroxide aqueous solution was added thereto and then extracted with ethyl acetate. It was washed with water and brine successively, and dried over anhydrous sodium sulfate. After concentration, the resulting residue was purified by silica gel chromatography, to give 0.36 g of the title compound.

$^1$H-NMR(400 MHz, CDCl$_3$) d; 8.16(s,1H), 7.97(d,J=5, 1H) 7.14(d,J=5,1H), 6.98(d,J=8,1H), 6.65(d,J=8,1H), 4.18 (brs,2H) 2.42(s,3H), 2.31(s,3H).

Production Example 26

1,2-Dimethyl-8-azaphenothiazine 0.36 g of 2-bromo-3,4-dimethylphenyl-3-amino-4-pyridinylsulfide obtained in Production Example 25, 0.28 g of copper(I) bromide and 0.37 g of sodium carbonate were reacted in 5 ml of dimethylsulfoxide at an external temperature of 200° C. for 2 hours. After adding ice-cold water and an ethylenediamine aqueous solution thereto, it was extracted with ethyl acetate. It was washed with water and brine successively, and dried over anhydrous sodium sulfate. After concentration, the resulting residue was perified by silica gel chromatography to give 0.20 g of the title compound.

$^1$H-NMR(400 MHz, CDCl$_3$) d; 7.96(d,J=5,1H), 7.84(s, 1H), 6.86(d,J=5,1H), 6.71(d,J=8,1H), 6.68(d,J=8,1H), 5.82 (brs,1H) 2.22(s,3H), 2.14(s,3H).

The following compounds were synthesized by applying the procedures in Production Example 5, Production Example 6, Production Example 7, Example 3 and Example 4 or the procedures in Production Example 5, Production Example 6 and Example 1 to 1,2-dimethyl-8-azaphenothiazine obtained in Production Example 26.

TABLE 11

| Ex. No. | | ¹H-NMR (400 MHz) δ |
|---|---|---|
| 36 | (structure) | CDCl₃<br>8.84(s, 1H), 8.45(d, J=5, 1H), 7.67(d, J=5, 1H), 7.38(d, J=8, 1H), 7.30–7.16(m, 6H), 4.26–4.08(m, 2H), 3.62(s, 2H), 2.52(t, J=7, 2H), 2.40(s, 3H), 2.38(s, 3H), 1.72–1.60(m, 2H), |
| 37 | (structure) | CDCl₃<br>8.87(s, 1H), 8.46(d, J=5, 1H), 7.67(d, J=5, 1H), 7.53(d, J=8, 1H), 7.21(d, J=8, 1H), 6.79(dd, J=B, 2, 1H), 6.71(t, J=8, 1H), 6.55(dd, J=8, 2, 1H), 4.28(m, 1H), 4.10(m, 1H), 3.87(s, 3H), 3.87(d, J=14, 1H), 3.82(d, J=14, 1H), 2.58–2.50(m, 2H), 2.40(s, 3H), 2.38(s, 3H) 1.80–1.70(m, 2H) |
| 38 | (structure) | CDCl₃<br>8.83(s, 1H), 8.44(d, J=5, 1H), 7.67(d, J=5, 1H), 7.57(d, J=8, 1H), 7.23–6.96(m, 5H), 4.22–4.06(m, 2H), 3.72(s, 2H), 2.61(s, 6H), 2.51(t, J=7, 2H), 2.39(s, 3H), 2.37(s, 3H), 1.70–1.60(m, 2H), |
| 39 | (structure) | CDCl₃<br>8.85(s, 1H), 8.44(d, J=5, 1H), 7.67(d, J=5, 1H), 7.58(d, J=8, 1H), 7.32–7.20(m, 6H), 4.22–4.06(m, 2H), 3.46(s, 2H), 2.40(s, 3H), 2.38 (s, 3H), 2.50–2.10(m, 10H), 1.70–1.50(m, 2H), |

TABLE 11-continued

| Ex. No. | | $^1$H-NMR (400 MHz) δ |
|---|---|---|
| 40 | (structure) | CDCl$_3$<br>8.93(s, 1H), 8.46(d, J=5, 1H), 8.44(d, J=4, 1H), 7.65(d, J=5, 1H), 7.56(d, J=8, 1H), 7.29–7.13(m, 4H), 4.46(m, 1H), 4.23(m, 1H), 3.96(d, J=14, 1H), 3.92(d, J=14, 1H), 2.81(t, J=7, 2H), 2.44(s, 3H), 2.41(s, 3H), 2.06–1.86(m, 2H) |
| 41 | (structure) | CDCl$_3$<br>8.90(s, 1H), 8.46(brs, 1H), 7.68(d, J=5, 1H), 7.58(d, J=8, 1H), 7.21(d, J=8, 1H), 7.00–6.60(m, 3H), 4.16–4.05(m, 2H), 3.85(s, 2H), 2.56(t, J=7, 2H), 2.42(s, 3H), 2.40(s, 3H), 1.82–1.74(m, 2H), |

Production Example 27

2-Amino-6-ethoxy-3-nitropyridine

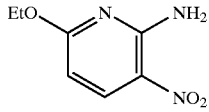

2.4 g of 60% sodium hydride was slowly added to 100 ml of ethanol and stirred as it was at room temperature for 10 minutes. 10 g of 2-amino-6-chloro-3-nitropyridine was added thereto and reacted at room temperature for 30 minutes. After concentration, water was added thereto, and it was extracted with ethyl acetate. It was washed with water and brine sucsessively, and dried over anhydrous sodium sulfate. After concentration, 9.7 g of the title compound was obtained.

$^1$H-NMR(400 MHz, CDCl$_3$) d; 8.28(d,J=9,1H), 6.11(d,J=9,1H), 4.36(q,J=7,2H), 1.38(t,J=7,3H).

Production Example 28

2-Amino-5-bromo-6-ethoxy-3nitropyridine

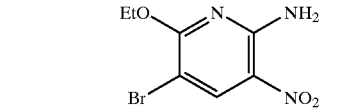

9.7 of 2-amino-6-ethoxy-3-nitropyridine obtained in Production Example 27 and 15 ml of triethylamine were dissolved in 200 ml of dichloromethane, and 2.2 ml of bromine was added thereto, followed by reacting at room temperature for 1 hour. After 2.2 ml of bromine was further added thereto and reacted for 1 hour, it was washed with water and brine successively, and dried over anhydrous sodium sulfate. After concentration, the resulting residue was purified by silica gel chromatography, to give 9.2 g of the title compound.

$^1$H-NMR(400 MHz, CDCl$_3$) d; 8.53(s,1H), 4.44(q,J=7, 2H), 1.43(t,J=7,3H).

Production Example 29

5-Bromo-2-chloro-6-ethoxy-3-nitropyridine

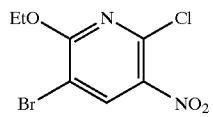

6.1 g of 2-amino-5-bromo-6-ethoxy-3-nitropyridine obtained in production Example 28, 4.7 g of copper(I) chloride and 5 g of t-butyl nitrite were added to 120 ml of acetonitrile and reacted at an external temperature of 65° C. for 1.5 hours. After adding ethyl acetate thereto, it was washed with diluted aqueous hydrochloric acid and brine successively, and dried over anhydrous sodium sulfate. After concentration, the resulting residue was purified by silica gel chromatography, to give 2.96 g of the title compound.

$^1$H-NMR(400 MHz, CDCl$_3$) d; 8.51(s,1H), 4.56(q,J=7, 2H), 1.46(t,J=7,3H).

Production Example 30

2,3-Dimethylphenyl-3-bromo-6-ethoxy-3-nitro-2-pyridinylsulfide

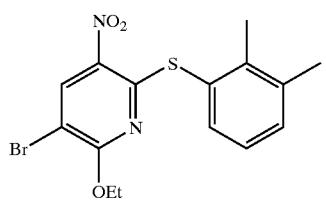

The title compound was obtained from 5-bromo-2-chloro-6-ethoxy-3-nitropyridine obtained in Production Example 29 in the same manner as in Production Example 20.

$^1$H-NMR(400 MHz, CDCl$_3$) d; 8.63 (s,1H), 7.37 (d,J=8, 1H) 7.26(d,J=8,1H), 7.14(t,J=8,1H), 3.77(q,J=7,2H), 2.34(s, 3H), 2.31(s,3H), 0.97(t,J=7,3H).

Production Example 31

8-Bromo-7-ethoxy-1,2-dimethyl-6azaphenothiazine

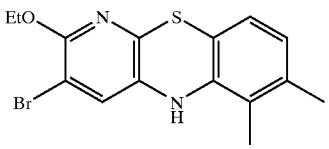

The title compound was obtained from 2,3-dimethylphenyl-5-bromo-6-ethoxy-3-nitro-2-pyridinylsulfide obtained in Production Example 30 in the same manner as in Production Example 21.

$^1$H-NMR(400 MHz, CDCl$_3$) d; 7.02(s,1H), 6.73(d,J=8, 1H), 6.66(d,J=8,1H), 5.45(brs,1H), 4.32(q,J=7,2H), 2.21(s, 3H), 2.08(s,3H), 1.38(t,J=7,3H).

Production Example 32

8-Cyano-7-ethoxy-1,2-dimethyl-6azaphenothiazine

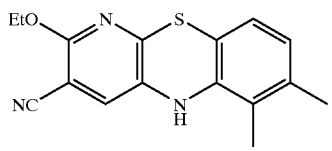

0.23 g of 8-bromo-7-ethoxy-1,2-dimethyl-6-azaphenothiazine obtained in Production Example 31 and 0.2 g of copper cyanide were reacted in 5 ml of hexamethylphosphoamide (HMPA) at an external temperature of 180° C. for 2 hours. Ice and aqueous ammonia were added thereto, and it was extracted with ethyl acetate. It was washed with water and brine successively, and dried over anhydrous sodium sulfate. After concentration, the resulting residue was purified by silica gel chromatography, to give 0.33 g of the title compound (containing a slight amount of HMPA).

$^1$H-NMR(400 MHz, CDCl$_3$) d; 6.98(s,1H), 6.67 (d,J=8, 1H), 6.64(d,J=8,1H), 5.78(brs,1H), 4.36(q,J=7,2H), 2.17(s, 6H), 1.38(t,J=7,3H).

Example 42

10-(3-Benzylaminopropyl)-8-cyano-7-ethoxy-1,2-dimethyl-6azaphenothiazine

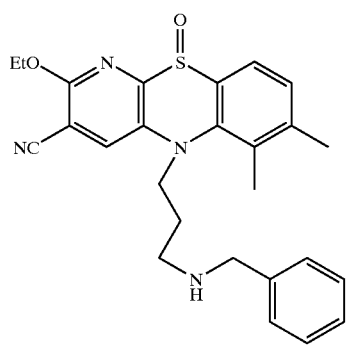

The title compound was synthesized by applying the procedures in Production Example 5, Production Example 6, Production Example 7, Example 3 and Example 4 or the procedures in Production Example 5, Production Example 6 and Example 1 to 8-cyano-7-ethoxy-1,2-dimethyl-6-azaphenothiazine obtained in Production Example 32.

The following compounds were synthesized in similar manners as in Production Examples 27 to 32 and Example 42.

TABLE 12
| Ex. No. | | ¹H-NMR (400 MHz) δ |
|---|---|---|
| 43 | 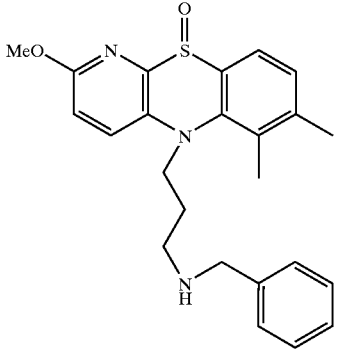 | CDCl₃<br>7.85(d, J=9, 1H), 7.59(d, J=8, 1H), 7.32–7.20(m, 5H), 7.16(d, J=8, 1H), 6.9(d, J=9, 1H), 4.26(m, 1H), 4.05(m, 1H), 4.01(s, 3H), 3.66(s, 2H), 2.60–2.52(m, 2H), 2.41(s, 3H), 2.39(s, 3H), 1.82–1.68(m, 2H) |
| 44 | 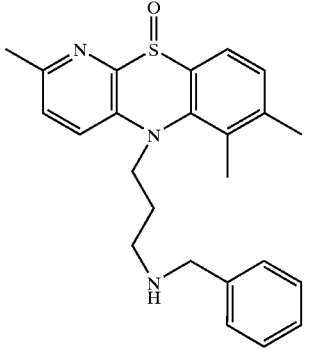 | CDCl₃<br>7.76(d, J=8, 1H), 7.63(d, J=8, 1H), 7.32–7.19(m, 6H), 7.16(d, J=8, 1H), 4.28(m, 1H), 4.07(m, 1H), 3.65(d, J=20, 1H), 3.60(d, J=20, 1H), 2.60(s, 3H), 2.53(t, J=7, 2H), 2.39(s, 3H), 2.38(s, 3H), 1.81–1.65(m, 2H), |
| 45 | 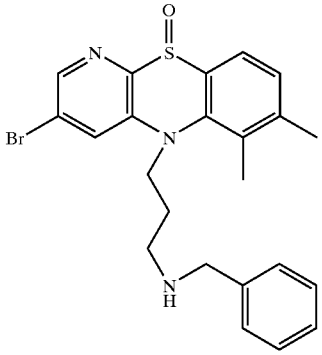 | CDCl₃<br>8.44(d, J=2, 1H), 8.01(d, J=2, 1H), 7.64(d, J=8, 1H), 7.32–7.18(m, 6H), 4.28(m, 1H), 4.13(m, 1H), 3.65(d, J=13, 1H), 3.61(d, J=13, 1H), 2.55(t, J=7, 2H), 2.39(s, 3H), 2.38(s, 3H), 1.80–1.65(m, 2H) |
| 46 | 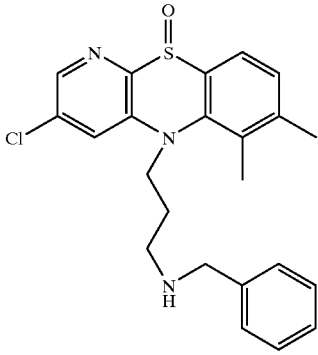 | CDCl₃<br>8.36(d, J=2, 1H), 7.86(d, J=2, 1H), 7.65(d, J=8, 1H), 7.32–7.12(m, 6H), 4.27(m, 1H), 4.12(m, 1H), 3.63(s, 2H), 2.56(t, J=7, 2H), 2.40(s, 3H), 2.39(s, 3H), 1.85–1.62(m, 2H) |

TABLE 12-continued
| Ex. No. | | ¹H-NMR (400 MHz) δ |
|---|---|---|
| 47 | 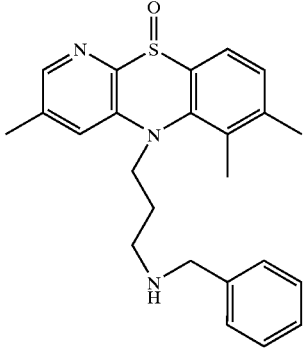 | CDCl₃<br>8.25(m, 3H), 7.66(m, 1H), 7.63(d, J=8, 1H), 7.31–7.19(m, 5H), 7.17(d, J=8, 1H), 4.31(m, 1H), 4.06(m, 1H), 3.63(s, 2H), 2.55(t, J=7, 1H), 2.44(s, 3H), 2.39(s, 3H), 2.38(s, 3H), 1.52–1.67 (m, 2H), |
| 48 | 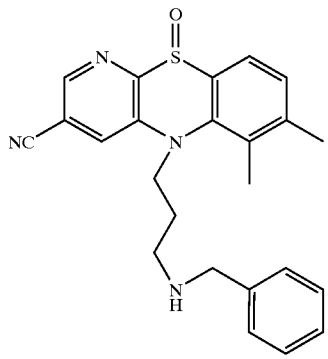 | CDCl₃<br>8.60(d, J=, 1H), 8.08(d, J=2, 1H), 7.66(d, J=8, 1H), 7.32–7.16(m, 6H), 4.30(m, 1H), 4.13(m, 1H), 3.62(s, 2H), 2.54(t, J=7, 2H), 2.41(s, 3H), 2.40(s, 3H), 1.72–1.60(m, 2H) |
| 49 | 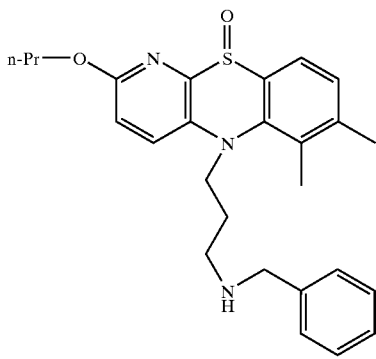 | CDCl₃<br>7.79(d, J=9, 1H), 7.60(d, J=8, 1H), 7.31–7.17(m, 5H), 7.15(d, J=8, 1H), 6.91(d, J=9, 1H), 4.40(m, 1H), 4.30(m, 1H), 4.24(m, 1H), 4.01(m, 1H), 3.62(s, 2H), 2.51(t, J=7, 2H), 2.40(s, 3H), 2.38(s, 3H), 1.90–1.60(m, 4H), 1.03(t, J=7, 3H) |
TABLE 13
| Ex. No. | | ¹H-NMR (400 MHz) δ |
|---|---|---|
| 50 | 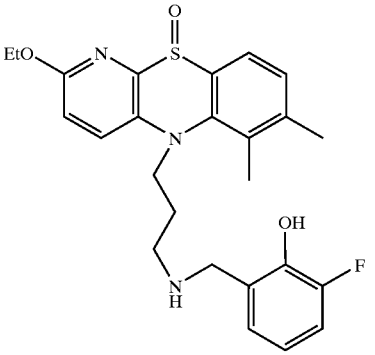 | CDCl₃<br>7.80(d, J=8, 1H), 7.60(d, J=8, 1H), 7.15(d, J=8, 1H), 6.96–6.88(m, 2H), 6.67–6.60(m, 2H), 4.56–4.36(m, 2H), 4.26–4.18(m, 1H), 3.98–3.90(m, 1H), 3.82(q, J=8, 2H), 2.50(t, J=7, 2H), 2.40(s, 6H), 1.78–1.68(m, 2H), 1.40(t, J=8, 3H) |

TABLE 13-continued

| Ex. No. | ¹H-NMR (400 MHz) δ |
|---|---|
| 51 | CDCl₃<br>7.79(d, J=8, 1H), 7.60(d, J=8, 1H), 7.15(d, J=8, 1H), 6.90(d, J=8, 1H), 6.78(d, J=8, 1H), 6.69(t, J=8, 1H), 6.53(d, J=8, 1H), 4.53–4.35(m, 2H), 4.25–4.14(m, 1H), 3.98–3.73(m, 6H), 2.57–2.43(m, 2H), 2.38(s, 6H), 1.78–1.63(m, 2H), 1.40(t, J=8, 3H) |
| 52 | CDCl₃<br>7.79(d, J=9, 1H), 7.60(d, J=8, H), 7.32–7.17(m, 5H), 7.15(d, J=8, 1H), 6.90(d, J=9, 1H), 4.9(m, 1H), 4.42(m, 1H), 4.20(m, 1H), 4.03(m, 1H), 3.61(s, 2H), 2.51(t, J=7, 2H), 2.40(s, 3H), 2.38(s, 3H), 1.75–1.65(m, 2H), 1.41(t, J=7, 3H) |
| 53 | CDCl₃<br>8.07(s, 1H), 7.59(d, J=9, 1H), 7.30–7.18(m, 5H), 7.16(d, J=8, 1H), 4.59–4.40(m, 2H), 4.13(m, 1H), 4.03(m, 1H), 3.64(d, J=13, 1H), 3.60(d, J=13, 1H), 2,51(t, J=7, 1H), 2.38(s, 6H), 1.75–1.60(m, 2H), 1.46(t, J=7, 3H) |
| 54 | CDCl₃<br>8.04(s, 1H), 7.64(d, J=8, 1H), 7.32–7.10(m, 6H), 4.30–4.10(m, 2H), 3.62(s, 2H), 2.80(s, 3H), 2.53(t, J=7, 2H), 2.40(s, 3H), 2.39(s, 3H), 1.75–1.60(m, 2H) |

TABLE 13-continued

| Ex. No. | | ¹H-NMR (400 MHz) δ |
|---|---|---|
| 55 | 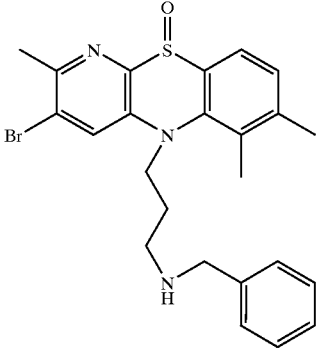 | CDCl₃<br>8.01(s, 1H), 7.62(d, J=8, 1H), 7.30–7.10(m, 6H), 4.23(m, 1H), 4.09(m, 1H), 3.62(s, 2H), 2.70(s, 3H), 2.53(t, J=7, 2H), 2.38(s, 6H), 1.80–1.60(m, 2H) |

Production Example 33

10H-Pyrazino[2,3-b][1,4]benzothiazine

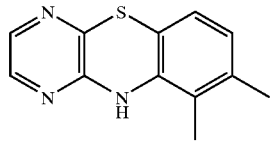

1.9 g of 2,3-dichloropyrazine obtained in a method of a known literature and 2.0 g of 2-amino-3,4-dimethylthiophenol were dissolved in 20 ml of N,N-dimethylformamide and heated under stirring at 90° C. for 1 hour. After allowed to cool, ethyl acetate was added thereto. The organic layer was washed with brine, dried over anhydrous magnesium sulfate and then the solvent was evaporated. Methanol was added to the resulting crude crystals. The insoluble matters were collected by filtration and washed with methanol, to give 1.8 g of the title compound as dark yellow crystals.

¹H-NMR(400 MHz, CDCl₃) d; 7.69(d,J=3,1H), 7.57(d,J=3,1H), 6.67(s,2H), 6.41(s,1H), 2.20(S,3H), 2.10(s,3H).

The following compounds were synthesized by applying the procedures in Production Example 5, Production Example 6, Production Example 7, Example 3 and Example 4, or by applying the procedures in Production Example 5, Production Example 6 and Example 1 to 10H-pyrazino[2,3-b][1,4]benzothiazine obtained in Production Example 33.

TABLE 14

| Ex. No. | | ¹H-NMR (400 MHz) δ |
|---|---|---|
| 56 | 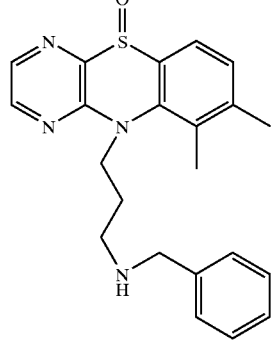 | CDCl₃<br>8.49(d, J=2, 1H), 8.32(d, J=2, 1H), 7.69(d, J=8, 1H), 7.28–7.16(m, 6H), 4.93–4.83(m, 1H), 4.20–4.10(m, 1H), 3.58(dd, J=3, 9, 2H), 2.55(t, J=7, 2H), 2.41(s, 3H), 2.40(s, 3H), 1.82–1.65(m, 2H) |
| 57 | 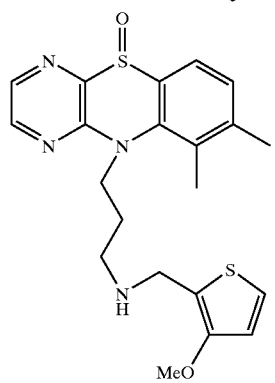 | CDCl₃<br>8.49(d, J=2, 1H), 8.31(d, J=2, 1H), 7.68(d, J=8), 7.23(d, J=8, 1H), 7.03(d, J=5, 1H), 6.77(d, J=5, 1H), 4.90–4.80(m, 1H), 4.22–4.10(m, 1H), 3.76(s, 3H), 3.68(dd, J=3, 9, 2H), 2.57(t, J=7, 2H), 2.42(s, 3H), 2.40(s, 3H), 1.80–1.60(m, 2H) |

The compound of the present invention is useful as a prophylactic or therapeutic agent for asthma, allergic coryza, atopic dermatitis, hay fever, allergic conjunctivitis or food allergy.

What is claimed is:

1. A compound represented by the formula (I), or a pharmacologically acceptable salt or hydrate thereof

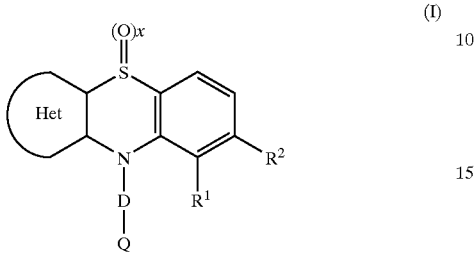

(I)

wherein

Het represents thiophene, thiazole, furan, pyridine, pyrimidine, pyrazine, pyrizadine, quinoline, isoquinoline or naphthyridine that may be substituted with from 1 to 3 substituents independently selected from the group defined by Z, wherein each Z is independently selected from the group consisting of a hydroxyl group, a lower alkyl group, a lower alkoxy group, a halogen atom, a cyano group, an acyl group, an amino group, a nitro group, a carboxyl group that may have a protective group, a carbamoyl group, an acylamino group, a sulfamoyl group, an alkylsulfonylamino group, an arylsulfonylamino group, a carboxyalkyl group, a carboxylalkoxy group, a methylenedioxy group, and an ethylenedioxy group;

$R^1$ and $R^2$ are the same as or different from each other, and each represents (1) a halogen atom,
(2) a lower alkyl group that may be substituted with 1 to 3 halogen atoms,
(3) a lower alkoxy group that may be substituted with 1 to 3 halogen atoms,
(4) a lower alkoxy lower alkyl group,
(5) a cyano group,
(6) a carbamoyl group that may have 1 or 2 substituents on the nitrogen atom thereof, wherein said substituents are independently selected from the group defined by Z above, or
(7) a carboxyl group that may have a protective group, wherein $R^1$ and $R^2$ may form a ring along with the carbon atoms to which they are bound, which ring may contain an oxygen atom, a sulfur atom or a nitrogen atom;

D represents a lower alkylene chain, a lower alkenylene chain, a lower alkynylene chain, or

wherein m and l each represents an integer of from 0 to 6, and ring A represents a hydrocarbon ring;

Q represents (1) a carbamoyl group that may have 1 or 2 substituents on the nitrogen atom thereof, wherein said substituents are independently selected from the group defined by Z above,
(2) an acyl group,
(3) an acyl lower alkyl group,
(4) a carboxyl group that may have a protective group, or
(5) the formula $-NR^{20}R^{21}$, wherein $R^{20}$ and $R^{21}$ are the same as or different from each other, and each represents (a) a hydrogen atom,
(b) a lower alkyl group that may be substituted with a halogen atom,
(c) a lower alkoxy group that may be substituted with 1 to 3 halogen atoms,
(d) a lower alkyl group that is substituted with a hydroxyl group,
(e) a lower alkoxy lower alkyl group,
(f) an aryl group that may have a substituent selected from the group defined by Z above,
(g) an aryl lower alkyl group that may have a substituent selected from the group defined by Z above,
(h) a monocyclic or condensed ring heteroaryl group containing from 1 to 4 of at least one selected from the group consisting of a sulfur atom, an oxygen atom and a nitrogen atom, which heteroaryl group may have a substituent selected from the group defined by Z above,
(i) a monocyclic or condensed ring heteroaryl lower alkyl group containing from 1 to 4 of at least one selected from the group consisting of a sulfur atom, an oxygen atom and a nitrogen atom, which heteroaryl lower alkyl group may have a substituent selected from the group defined by Z above,
(j) an aryloxy group,
(k) an aryl lower alkoxy group that may have a substituent selected from the group defined by Z above,
(l) a heteroaryloxy group that may have a substituent selected from the group defined by Z above,
(m) a heteroaryl lower alkoxy group that may have a substituent selected from the group defined by Z above,
(n) a carboxyalkyl group that may have a protective group,
(o) an acyl group,
(p) an acyl lower alkyl group,
(q) an acylamino group,
(r) an acylamino lower alkyl group,
(s) a carbamoyl lower alkyl group that may have a substituent selected from the group defined by Z above,
(t) an amino lower alkyl group,
(u) a cyano lower alkyl group,
(v) an acyl lower alkyl group,
(w) a lower cycloalkyl group,
(x) a lower cycloalkyl lower alkyl group, or
(y) an amidino group that may be substituted with a lower alkyl group, wherein $R^{20}$ and $R^{21}$ may form a 3- to 8-membered ring along with the nitrogen atom to which they are bound, and the ring may have, as a component constituting the ring, in addition to the carbon atoms, at least one selected from the group consisting of a nitrogen atom, a sulfur atom, an oxygen atom and the formula $-NR^{22}$, wherein $R^{22}$ represents
  (1) a hydrogen atom,
  (2) a lower alkyl group that may be substituted with 1 to 3 halogen atoms,
  (3) an acyl group,
  (4) an acyl lower alkyl group,
  (5) an aryl group that may have a substituent selected from the group defined by Z above,
  (6) a monocyclic or condensed ring heteroaryl group containing from 1 to 4 of at least one selected from the group consisting of a sulfur atom, an oxygen atom and a nitrogen atom, which heteroaryl group may have a substituent selected from the group defined by Z above,
  (7) an arylalkyl group that may have a substituent selected from the group defined by Z above,
  (8) a monocyclic or condensed ring heteroarylalkyl group containing 1 to 4 of at least one selected from the group consisting of a sulfur atom, an oxygen atom and a nitrogen atom, which heteroarylalkyl group may have a substituent selected from the group defined by Z above, or
  (9) the formula $-S(O)_s-(Y)_u-R^{23}$, wherein $R^{23}$ represents
    (a) a hydrogen atom,
    (b) a lower alkyl group that may be substituted with 1 to 3 halogen atoms, or
    (c) an aryl group that may have a substituent selected from the group defined by Z above,
  Y represents a methylene chain,
  s represents an integer of from 0 to 2, and
  u represents 0 or 1; and
x represents an integer of from 0 to 2.

2. The compound as claimed in claim 1, or a pharmacologically acceptable salt or hydrate thereof, wherein $R^1$ and $R^2$ are the same as or different from each other, and each represents halogen atom, a lower alkyl group that may be substituted with 1 to 3 halogen atoms, a lower alkoxy group that may be substituted with 1 to 3 halogen atoms or a lower alkoxy lower alkyl group.

3. The compound as claimed in claim 1, or a pharmacologically acceptable salt or hydrate thereof, wherein
  Q represents the formula $-NR^{20}R^{21}$
    wherein $R^{20}$ and $R^{21}$ are the same as or different from each other, and each represents
      (a) a hydrogen atom,
      (b) a lower alkyl group,
      (c) a lower alkoxy group,
      (d) a lower alkyl group that is substituted with a hydroxyl group,
      (e) a lower alkoxy lower alkyl group,
      (f) an aryl group that may have a substituent,
      (g) an aryl lower alkyl group that may have a substituent,
      (h) a heteroaryl group that may have a substituent,
      (i) a heteroaryl lower alkyl group that may have a substituent,
      (j) a heteroaryl lower alkoxy group that may have a substituent,
      (k) a carboxy lower alkyl group that may have a protective group,
      (l) an acyl group,
      (m) an acylamino group that may have a substituent,
      (n) an acylamino lower alkyl group that may have a substituent,
      (o) an amino lower alkyl group that may have a substituent,
      (p) a cyano lower alkyl group,
      (q) an acyl lower alkyl group,
      (r) a lower cycloalkyl group, or
      (s) a lower cycloalkyl lower alkyl group, wherein $R^{20}$ and $R^{21}$ may form a 3- to 8-membered ring that may have a substituent along with the nitrogen atom to which they are bound, and the ring may have, as a component constituting the ring, in addition to the carbon atoms, a nitrogen atom, a sulfur atom, an oxygen atom or the formula $-NR^{22}$, and may be condensed with a benzene ring that may have a substituent, wherein in $-NR^{22}$,
    $R^{22}$ represents:
      (a) hydrogen atom,
      (b) a lower alkyl group that may be substituted with halogen,
      (c) an aryl group that may have a substituent,
      (d) a heteroaryl group that may have a substituent,
      (e) an aryl lower alkyl group that may have a substituent,
      (f) a heteroaryl lower alkyl group that may have a substituent, or
      (g) the formula $-S(O)_s-(Y)_u-R^{23}$, wherein
        $R^{23}$ represents hydrogen atom, a lower alkyl group that may be substituted with a halogen atom or an aryl group that may have a substituent,
        Y represents a methylene chain,
        s represents an integer of from 0 to 2, and
        u represents 0 or 1.

4. The compound as claimed in claim 1, or a pharmacologically acceptable salt or hydrate thereof, wherein Q represents the formula $-NR^{20}R^{21}$,
  i) $R^{20}$ and $R^{21}$ are the same as or different from each other, and each represents hydrogen atom, a lower alkyl group, a lower alkyl group that is substituted with a hydroxyl group, a lower alkoxy lower alkyl group, an aryl group that may have a substituent, an aryl lower alkyl group that may have a substituent, a heteroaryl group that may have a substituent, a heteroaryl lower alkyl group that may have a substituent, a carboxy lower alkyl group that may have a protective group, a cyano lower alkyl group or a lower cycloalkyl lower alkyl group;
  ii) a ring formed by $R^{20}$ and $R^{21}$ along with the nitrogen atom to which they are bound is a 5- or 6-membered ring that may have a substituent, and the ring is a ring that may have, as a component constituting the ring, in addition to the carbon atoms, at least one selected from the group consisting of a sulfur atom, an oxygen atom and the formula $-NR^{22}$, wherein
    $R^{22}$ represents hydrogen atom, a lower alkyl group that may be substituted with a halogen atom, an aryl group that may have a substituent, a heteroaryl group that may have a substituent, an aryl lower alkyl group that may have a substituent, a heteroaryl lower alkyl group that may have a substituent or the formula $-S(O)_s-(Y)_u-R^{23}$, wherein
    $R^{23}$ represents hydrogen atom, a lower alkyl group or an aryl group that may have a substituent,
    Y represents a methylene chain,
    s represents an integer of from 0 to 2 and
    u represents 0 or 1; or
  iii) a ring formed by $R^{20}$ and $R^{21}$ along with the nitrogen atom to which they are bound is tetrahydroquinoline, tetrahydroisoquinoline, indoline or isoindoline.

5. The compound as claimed in claim 1, or a pharmacologically acceptable salt or hydrate thereof, wherein $R^1$ and $R^2$ each represents a lower alkyl group.

6. The compound as claimed in claim 1, or a pharmacologically acceptable salt or hydrate thereof, wherein $R^1$ and $R^2$ are the same as or different from each other, and each represents a methyl group or an ethyl group.

7. The compound as claimed in claim 1, or a pharmacologically acceptable salt or hydrate thereof, wherein both $R^1$ and $R^2$ are methyl groups.

8. The compound as claimed in claim 1, or a pharmacologically acceptable salt or hydrate thereof, wherein Q is represented by the formula —$NR^{20}R^{21}$, wherein $R^{20}$ and $R^{21}$ are the same as or different from each other, and each represents hydrogen atom, a lower alkyl group, lower alkyl group that is substituted with a hydroxyl group, an alkoxyalkyl group, an aryl group that may have a substituent, an aryl lower alkyl group that may have a substituent, a heteroaryl group that may have a substituent, a heteroaryl lower alkyl group that may have a substituent, a carboxy lower alkyl group that may have a protective group, a cyano lower alkyl group or a cycloalkylalkyl group.

9. The compound as claimed in claim 1, or a pharmacologically acceptable salt or hydrate thereof, wherein the ring Het represents pyridine.

10. The compound as claimed in claim 1, or a pharmacologically acceptable salt or hydrate thereof, wherein the ring Het represents pyrazine.

11. The compound as claimed in claim 1, or a pharmacologically acceptable salt or hydrate thereof, wherein the ring Het represents pyrimidine.

12. The compound as claimed in claim 1, or a pharmacologically acceptable salt or hydrate thereof, wherein the ring Het represents thiophene.

13. The compound as claimed in claim 1, or a pharmacologically acceptable salt or hydrate thereof, wherein the ring Het represents thiazole.

14. The compound as claimed in claim 1, or a pharmacologically acceptable salt or hydrate thereof, wherein the ring Het represents pyridine or thiophene, and both $R^1$ and $R^2$ each represents methyl group.

15. The compound as claimed in claim 1, or a pharmacologically acceptable salt or hydrate thereof, wherein x is 1.

16. Compound as claimed in claim 1, or a pharmacologically acceptable salt or hydrate thereof, which is selected from the following compound group:
1) 10-[3-[(3-methoxy-2-thienyl)methylamino]propyl]-1,2-dimethyl-6-azaphenothiazine-5-oxide;
2) 10-[3-[(2,4-dichlorophenyl)methylamino]propyl]-1,2-dimethyl-6-azaphenothiazine-5-oxide;
3) 10-(3-benzylaminopropyl)-8-cyano-7-ethoxy-1,2-dimethyl-6-azaphenothiazine-5-oxide;
4) 10-(3-benzylaminopropyl)-1,2-dimethyl-7-propoxy-6-azaphenothiazine-5-oxide; and
5) 10-(3-benzylaminopropyl)-7-ethoxy-1,2-dimethyl-6-azaphenothiazine-5-oxide.

17. A pharmaceutical composition, comprising:
the compound as claimed in claim 1, or a pharmacologically acceptable salt or hydrate thereof, as an active component; and
a pharmaceutically acceptable carrier.

18. A method for prevention and remedy of asthma, allergic coryza, atopic dermatitis, hay fever, allergic conjunctivitis and/or food allergy, which comprises administering a pharmacologically or clinically effective amount of the compound as claimed in claim 1, or a pharmacologically acceptable salt or hydrate thereof to a patient in need thereof.

19. A method for prevention and remedy of disease, against which a tyrosine kinase inhibiting action is effective, which comprises the step of
administering a pharmacologically or clinically effective amount of the compound as claimed in claim 1, or a pharmacologically acceptable salt or hydrate thereof, to a patient infected with disease, against which a tyrosine kinase inhibiting action is effective, wherein the disease, against which a tyrosine kinase inhibiting action is effective, is allergy, disease against which an antiallergenic action is effective, asthma, allergic coryza, atopic dermatitis, hay fever, allergic conjunctivitis and food allergy.

20. The compound as claimed in claim 1, wherein Het may be substituted with from 1 to 3 substituents independently selected from the group consisting of a hydroxyl group, a lower alkyl group, a lower alkoxy group, a halogen atom, a cyano group, an acyl group, an amino group, a nitro group, a carboxyl group, a carbamoyl group, an acylamino group, a sulfamoyl group, an alkylsulfonylamino group, an arylsulfonylamino group, a carboxyalkyl group, a carboxylalkoxy group, a methylenedioxy group, and an ethylenedioxy group.

21. The compound as claimed in claim 1, wherein said carbamoyl group (6) of $R^1$ and $R^2$ may have 1 or 2 substituents on the nitrogen atom thereof, said substituents being selected from the group consisting of a hydroxyl group, a lower alkyl group, a lower alkoxy group, a halogen atom, a cyano group, an acyl group, an amino group, a nitro group, a carboxyl group, a carbamoyl group, an acylamino group, a sulfamoyl group, an alkylsulfonylamino group, an arylsulfonylamino group, a carboxyalkyl group, a carboxylalkoxy group, a methylenedioxy group, and an ethylenedioxy group.

22. The compound as claimed in claim 1, wherein said carbamoyl group (1) of Q may have a substituent selected from the group consisting of a hydroxyl group, a lower alkyl group, a lower alkoxy group, a halogen atom, a cyano group, an acyl group, an amino group, a nitro group, a carboxyl group, a carbamoyl group, an acylamino group, a sulfamoyl group, an alkylsulfonylamino group, an arylsulfonylamino group, a carboxyalkyl group, a carboxylalkoxy group, a methylenedioxy group, and an ethylenedioxy group.

23. The compound as claimed in claim 1, wherein said heteroaryl group (5) of Q may have a substituent selected from the group consisting of a hydroxyl group, a lower alkyl group, a lower alkoxy group, a halogen atom, a cyano group, an acyl group, an amino group, a nitro group, a carboxyl group, a carbamoyl group, an acylamino group, a sulfamoyl group, an alkylsulfonylamino group, an arylsulfonylamino group, a carboxyalkyl group, a carboxylalkoxy group, a methylenedioxy group, and an ethylenedioxy group.

24. The compound as claimed in claim 1, wherein said aryl group (f) of $R^{20}$ and $R^{21}$ may have a substituent selected from the group consisting of a hydroxyl group, a lower alkyl group, a lower alkoxy group, a halogen atom, a cyano group, an acyl group, an amino group, a nitro group, a carboxyl group, a carbamoyl group, an acylamino group, a sulfamoyl group, an alkylsulfonylamino group, an arylsulfonylamino group, a carboxyalkyl group, a carboxylalkoxy group, a methylenedioxy group, and an ethylenedioxy group.

25. The compound as claimed in claim 1, wherein said heteroaryl group (h) of $R^{20}$ and $R^{21}$ contains from 1 to 4 of at least one selected from the group consisting of a sulfur atom, an oxygen atom and a nitrogen atom, which heteroaryl group may have a substituent selected from the group consisting of a hydroxyl group, a lower alkyl group, a lower alkoxy group, a halogen atom, a cyano group, an acyl group, an amino group, a nitro group, a carboxyl group, a carbamoyl group, an acylamino group, a sulfamoyl group, an alkylsulfonylamino group, an arylsulfonylamino group, a carboxyalkyl group, a carboxylalkoxy group, a methylenedioxy group, and an ethylenedioxy group.

26. The compound as claimed in claim 1, wherein in the formula —NR$^{22}$, R$^{22}$ may be an aryl group (5) that may have a substituent selected from the group consisting of a hydroxyl group, a lower alkyl group, a lower alkoxy group, a halogen atom, a cyano group, an acyl group, an amino group, a nitro group, a carboxyl group, a carbamoyl group, an acylamino group, a sulfamoyl group, an alkylsulfonylamino group, an arylsulfonylamino group, a carboxyalkyl group, a carboxylalkoxy group, a methylenedioxy group, and an ethylenedioxy group.

27. The compound as claimed in claim 1, wherein in the formula —NR$^{22}$, when R$^{22}$ may be a heteroaryl group (6), said heteroaryl group is a monocyclic or condensed ring heteroaryl group containing from 1 to 4 of at least one selected from the group consisting of a sulfur atom, an oxygen atom and a nitrogen atom, which heteroaryl group may have a substituent selected from the group consisting of a hydroxyl group, a lower alkyl group, a lower alkoxy group, a halogen atom, a cyano group, an acyl group, an amino group, a nitro group, a carboxyl group, a carbamoyl group, an acylamino group, a sulfamoyl group, an alkylsulfonylamino group, an arylsulfonylamino group, a carboxyalkyl group, a carboxylalkoxy group, a methylenedioxy group, and an ethylenedioxy group.

28. The compound as claimed in claim 1, wherein in the formula —NR$^{22}$, when R$^{22}$ may be an arylalkyl group (7), said arylalkyl group may have a substituent selected from the group consisting of a hydroxyl group, a lower alkyl group, a lower alkoxy group, a halogen atom, a cyano group, an acyl group, an amino group, a nitro group, a carboxyl group, a carbamoyl group, an acylamino group, a sulfamoyl group, an alkylsulfonylamino group, an arylsulfonylamino group, a carboxyalkyl group, a carboxylalkoxy group, a methylenedioxy group, and an ethylenedioxy group.

29. The compound as claimed in claim 1, wherein in the formula —NR$^{22}$$_1$ when R$^{22}$ may be a heteroarylalkyl group (8), said heteroarylalkyl group is a monocyclic or condensed ring heteroarylalkyl group containing 1 to 4 of at least one selected from the group consisting of a sulfur atom, an oxygen atom and a nitrogen atom, which heteroarylalkyl group may have a substituent selected from the group consisting of a hydroxyl group, a lower alkyl group, a lower alkoxy group, a halogen atom, a cyano group, an acyl group, an amino group, a nitro group, a carboxyl group, a carbamoyl group, an acylamino group, a sulfamoyl group, an alkylsulfonylamino group, an arylsulfonylamino group, a carboxyalkyl group, a carboxylalkoxy group, a methylenedioxy group, and an ethylenedioxy group.

30. The compound as claimed in claim 1, wherein in the formula —S(O)$_s$—(Y)$_u$—R$^{23}$, when R$^{23}$ represents an aryl group (c), said aryl group may have a substituent selected from the group consisting of a hydroxyl group, a lower alkyl group, a lower alkoxy group, a halogen atom, a cyano group, an acyl group, an amino group, a nitro group, a carboxyl group, a carbamoyl group, an acylamino group, a sulfamoyl group, an alkylsulfonylamino group, an arylsulfonylamino group, a carboxyalkyl group, a carboxylalkoxy group, a methylenedioxy group, and an ethylenedioxy group.

31. A compound represented by the formula (I), or a pharmacologically acceptable salt or hydrate thereof

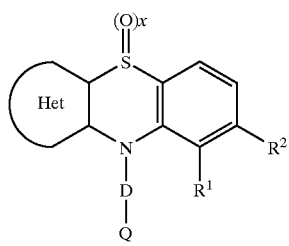

(I)

wherein

Het represents thiophene, thiazole, furan, pyridine, pyrimidine, pyrazine, pyrizadine, quinoline, isoquinoline or naphthyridine that may be substituted with from 1 to 3 substituents independently selected from the group defined by Z;

R$^1$ and R$^2$ are the same as or different from each other, and each represents
(1) a halogen atom,
(2) a lower alkyl group that may be substituted with 1 to 3 halogen atoms,
(3) a lower alkoxy group that may be substituted with 1 to 3 halogen atoms,
(4) a lower alkoxy lower alkyl group,
(5) a cyano group,
(6) a carbamoyl group that may have 1 or 2 substituents on the nitrogen atom thereof, wherein said substituents are independently selected from the group defined by Z, or
(7) a carboxyl group wherein R$^1$ and R$^2$ may form a ring along with the carbon atoms to which they are bound, which ring may contain an oxygen atom, a sulfur atom or a nitrogen atom;

D represents a lower alkylene chain, a lower alkenylene chain, a lower alkynylene chain or

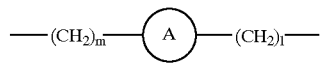

wherein m and l each represents an integer of from 0 to 6, and ring A represents a hydrocarbon ring or a heterocyclic ring;

Q represents
(1) a carbamoyl group that may have a substituent selected from the group defined by Z,
(2) an acyl group,
(3) an acyl lower alkyl group,
(4) a carboxyl group,
(5) a heteroaryl group that may have a substituent selected from the group defined by Z, or
(6) the formula —NR$^{20}$R$^{21}$, wherein
R$^{20}$ and R$^{21}$ are the same as or different from each other, and each represents
(a) a hydrogen atom,
(b) a lower alkyl group that may be substituted with a halogen atom,
(c) a lower alkoxy group that may be substituted with 1 to 3 halogen atoms,
(d) a lower alkyl group that is substituted with a hydroxyl group,
(e) a lower alkoxy lower alkyl group,
(f) an aryl group that may have a substituent selected from the group defined by Z, (g) an aryl lower alkyl group,
(h) a monocyclic or condensed ring heteroaryl group containing from 1 to 4 of at least one selected from the group consisting of a sulfur atom, an oxygen atom and a nitrogen atom, which heteroaryl group may have a substituent selected from the group defined by Z,
(i) a heteroaryl lower alkyl group,
(j) an aryloxy group,
(k) an aryl lower alkoxy group,
(l) a heteroaryloxy group,
(m) a heteroaryl lower alkoxy group,
(n) a carboxyalkyl group that may have a protective group,
(o) an acyl group,
(p) an acyl lower alkyl group,
(q) an acylamino group,
(r) an acylamino lower alkyl group,
(s) a carbamoyl lower alkyl group,
(t) an amino lower alkyl group,
(u) a cyano lower alkyl group,
(v) an acyl lower alkyl group,
(w) a lower cycloalkyl group,
(x) a lower cycloalkyl lower alkyl group, or
(y) an amidino group that may be substituted with a lower alkyl group,
wherein $R^{20}$ and $R^{21}$ may form a 3- to 8-membered ring along with the nitrogen atom to which they are bound, and the ring may have, as a component constituting the ring, in addition to the carbon atoms, at least one selected from the group consisting of a nitrogen atom, a sulfur atom, an oxygen atom and the formula —$NR^{22}$,
wherein $R^{22}$ represents
(1) a hydrogen atom,
(2) a lower alkyl group that may be substituted with 1 to 3 halogen atoms,
(3) an acyl group,
(4) an acyl lower alkyl group,
(5) an aryl group that may have a substituent selected from the group defined by Z,
(6) a monocyclic or condensed ring heteroaryl group containing from 1 to 4 of at least one selected from the group consisting of a sulfur atom, an oxygen atom and a nitrogen atom, which heteroaryl group may have a substituent selected from the group defined by Z,
(7) an arylalkyl group that may have a substituent selected from the group defined by Z,
(8) a monocyclic or condensed ring heteroarylalkyl group containing 1 to 4 of at least one selected from the group consisting of a sulfur atom, an oxygen atom and a nitrogen atom, which heteroarylalkyl group may have a substituent selected from the group defined by Z, or
(9) the formula —$S(O)_s$—$(Y)_u$—$R^{23}$, wherein $R^{23}$ represents
(a) a hydrogen atom,
(b) a lower alkyl group that may be substituted with 1 to 3 halogen atoms, or
(c) an aryl group that may have a substituent selected from the group defined by Z,
Y represents a methylene chain,
s represents an integer of from 0 to 2, and
u represents 0 or 1; and
x represents an integer of from 0 to 2, wherein Z is selected from the group consisting of a hydroxyl group, a lower alkyl group, a lower alkoxy group, a halogen atom, a cyano group, an acyl group, an amino group, a nitro group, a carboxyl group, a carbamoyl group, an acylamino group, a sulfamoyl group, an alkylsulfonylamino group, an arylsulfonylamino group, a carboxyalkyl group, a carboxylalkoxy group, a methylenedioxy group, and an ethylenedioxy group.

* * * * *